United States Patent
Kang et al.

(10) Patent No.: US 11,435,826 B2
(45) Date of Patent: Sep. 6, 2022

(54) ELECTRONIC DEVICE AND CONTROL METHOD THEREOF

(71) Applicant: Samsung Electronics Co., Ltd., Suwon-si (KR)

(72) Inventors: Hyuk Kang, Yongin-si (KR); Jae-bong Yoo, Seongnam-si (KR); Duk-ki Hong, Seoul (KR); Kyung-soo Lim, Yongin-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 422 days.

(21) Appl. No.: 16/461,105

(22) PCT Filed: Nov. 16, 2017

(86) PCT No.: PCT/KR2017/013048
§ 371 (c)(1),
(2) Date: May 15, 2019

(87) PCT Pub. No.: WO2018/093183
PCT Pub. Date: May 24, 2018

(65) Prior Publication Data
US 2020/0064921 A1    Feb. 27, 2020

Related U.S. Application Data

(60) Provisional application No. 62/422,684, filed on Nov. 16, 2016.

(30) Foreign Application Priority Data

Apr. 11, 2017   (KR) .................... 10-2017-0046890
Nov. 16, 2017   (KR) .................... 10-2017-0153105

(51) Int. Cl.
*G06F 3/01*    (2006.01)
*G02B 27/01*   (2006.01)
(Continued)

(52) U.S. Cl.
CPC .............. *G06F 3/015* (2013.01); *A61B 5/377* (2021.01); *A61B 5/389* (2021.01); *A61B 5/398* (2021.01);
(Continued)

(58) Field of Classification Search
CPC .. G06F 21/44; G06F 2203/0381; G06F 21/32; G06F 3/015; G06F 3/038;
(Continued)

(56) References Cited

U.S. PATENT DOCUMENTS 4,474,186 A    10/1984  Ledley et al.
5,360,971 A    11/1994  Kaufman et al.
(Continued)

FOREIGN PATENT DOCUMENTS

CN    103310142 A    9/2013
CN    103809743 A    5/2014
(Continued)

OTHER PUBLICATIONS

Ghayoumi, M. (2015). A Review of Multimodal Biometric Systems: Fusion Methods and Their Applications. 2015 IEEE/ACIS 14th International Conference on Computer and Information Science (ICIS). Published. https://doi.org/10.1109/ICIS.2015.7166582 (Year: 2015).*

(Continued)

*Primary Examiner* — Christine H Matthews
*Assistant Examiner* — Joshua Daryl D Lannu
(74) *Attorney, Agent, or Firm* — Jefferson IP Law, LLP

(57) ABSTRACT

An electronic device is disclosed. The electronic device identifies a user on the basis of: a biological signal input unit for receiving the input of a user's biological signal detected through an electrode; a voice input unit for receiving the
(Continued)

input of a voice signal; a biological signal inputted through the biological signal input unit; and a voice signal inputted through a microphone.

11 Claims, 17 Drawing Sheets

(51) Int. Cl.
| G06F 3/16 | (2006.01) |
| H04R 1/08 | (2006.01) |
| G06F 21/32 | (2013.01) |
| G06F 21/44 | (2013.01) |
| A61B 5/053 | (2021.01) |
| A61B 5/25 | (2021.01) |
| A61B 5/377 | (2021.01) |
| A61B 5/389 | (2021.01) |
| A61B 5/398 | (2021.01) |

(52) U.S. Cl.
CPC ........... *G02B 27/017* (2013.01); *G06F 3/167* (2013.01); *G06F 21/32* (2013.01); *G06F 21/44* (2013.01); *H04R 1/08* (2013.01); *G02B 2027/0178* (2013.01)

(58) Field of Classification Search
CPC ......... G06F 3/167; A61B 5/377; A61B 5/389; A61B 5/398; G02B 2027/0178; G02B 27/01; G02B 27/017; H04R 1/08
See application file for complete search history.

(56) References Cited

U.S. PATENT DOCUMENTS

| 8,963,806 | B1 | 2/2015 | Starner et al. | |
| 9,503,800 | B2 | 11/2016 | Song et al. | |
| 9,594,892 | B2 | 3/2017 | Bae et al. | |
| 9,811,648 | B2 | 11/2017 | Choi et al. | |
| 10,032,008 | B2* | 7/2018 | Griffiths | G06F 21/305 |
| 2005/0102134 | A1 | 5/2005 | Manabe et al. | |
| 2005/0202844 | A1* | 9/2005 | Jabri | A61B 6/4494 |
| | | | | 455/556.1 |
| 2006/0061544 | A1 | 3/2006 | Min et al. | |
| 2010/0225443 | A1* | 9/2010 | Bayram | H04W 12/068 |
| | | | | 340/5.83 |
| 2011/0246187 | A1 | 10/2011 | Srinivasan et al. | |
| 2012/0016827 | A1* | 1/2012 | Evans | G07C 9/37 |
| | | | | 706/14 |
| 2013/0044055 | A1* | 2/2013 | Karmarkar | G06F 21/316 |
| | | | | 345/158 |
| 2014/0126782 | A1 | 5/2014 | Takai et al. | |
| 2014/0304792 | A1 | 10/2014 | Derchak et al. | |
| 2015/0074797 | A1 | 3/2015 | Choi et al. | |
| 2015/0242605 | A1* | 8/2015 | Du | G06F 21/32 |
| | | | | 726/7 |
| 2015/0341717 | A1 | 11/2015 | Song et al. | |
| 2016/0063231 | A1 | 3/2016 | Bae et al. | |
| 2016/0259986 | A1 | 9/2016 | Yun et al. | |
| 2016/0284363 | A1 | 9/2016 | Von Borstel et al. | |

FOREIGN PATENT DOCUMENTS

| CN | 105093526 A | 11/2015 |
| CN | 105389489 A | 3/2016 |
| CN | 105512534 A | 4/2016 |
| EP | 1637975 A | 3/2006 |
| JP | 2003-058269 A | 2/2003 |
| JP | 2005-293209 A | 10/2005 |
| KR | 10-0594117 B1 | 6/2006 |
| KR | 20-2009-0011127 U | 10/2009 |
| KR | 10-2015-0029105 A | 3/2015 |
| KR | 10-2015-0134666 A | 12/2015 |
| KR | 10-1633057 B1 | 6/2016 |

OTHER PUBLICATIONS

Monwar, M., & Gavrilova, M. (2009). Multimodal Biometric System Using Rank-Level Fusion Approach. IEEE Transactions on Systems, Man, and Cybernetics, Part B (Cybernetics), 39(4), 867-878. https://doi.org/10.1109/tsmcb.2008.2009071 (Year: 2009).*
European Office Action dated Feb. 27, 2020, issued in European Patent Application No. 17870975.4.
European Search Report dated Oct. 1, 2019; European Appln No. 17870975.4-1216 / 3518129 PCT/KR2017013048.
Chinese Office Action dated Mar. 30, 2022, issued in Chinese Application No. 201780070666.6.

* cited by examiner

ELECTRONIC DEVICE AND CONTROL METHOD THEREOF

TECHNICAL FIELD

The disclosure relates to an electronic device and a controlling method thereof, and more specifically to a wearable electronic device that may sense a biological signal of a user and a controlling method thereof.

BACKGROUND ART

Recently, as a research on a wearable device is vigorously performed, various wearable devices have been released. The wearable devices currently released or to be released may be a smart watch, a head mounted display (HMD) device, a smart belt, etc.

The HMD device is a wearable display device which is worn such as glasses and can display an image, and also called a Face Mounted Display (FMD) because this device disposes a display near eyes of a user. The HMD device can be combined with an augmented reality technology, an N screen technology, etc. over a simple display function for providing various conveniences to a user.

Especially, the HMD device may provide a surrounding image to provide a more realistic and practical virtual space to a user. The surrounding image may show visual information spread in all directions based on the HMD device. Accordingly, the HMD device may direct the direction to which a face of a user wearing the HMD device faces, and display the image corresponding to the corresponding direction from among the surrounding images. Accordingly, the user may feel like himself/herself actually exists in the virtual space.

Meanwhile, it is difficult to use an additional input device such as a keyboard or a mouse in the HMD device environment, and thus, the technology for detecting a biological signal of a user and controlling the HMD device by receiving the detected biological signal has been introduced. Especially, the user who wears the HMD device frequently requires a user authentication in various circumstances, and in this case, it is difficult for the user to perform a fingerprint recognition, a PIN input, a pattern input, etc. and thus, the user authentication has been performed by recognizing a voice according to the utterance of the user, and determining whether a specific word or a sentence has been uttered.

However, there have been problems that if a user authentication is performed using the voice signal of a user, the recognition rate is reduced in a noisy environment because of a sensitivity regarding the external noise, and it is difficult to confirm whether the voice has been uttered by the user wearing an HMD device.

DETAILED DESCRIPTION

Technical Problem

An embodiment is according to the above described needs and the purpose of the embodiment is to provide an electronic device that may increase the accuracy of a user authentication using a plurality of different signals generated from a user, and a controlling method thereof.

Technical Solution

According to an embodiment, there is provided an electronic device including a biological signal input unit configured to receive a biological signal of a user detected through an electrode, a voice input unit configured to receive a voice signal, and a processor configured to identify the user based on a biological signal input through the biological signal input unit and a voice signal input through the voice input unit.

The processor may generate a synthesis signal in which the input voice signal and the input biological signal are synthesized, and identify the user based on the generated synthesis signal.

The processor may generate the synthesis signal using a voice signal input through the voice input unit while the biological signal is detected and the detected biological signal.

The electronic device further includes a storage storing characteristic information of a synthesis signal in which a voice signal regarding a specific utterance of the user and a biological signal of the user are synthesized, and the processor may identify the user by extracting characteristic information of the generated synthesis signal and comparing the extracted characteristic information with characteristic information of a synthesis signal stored in the storage.

The electronic device further includes a storage storing characteristic information of a voice signal regarding a specific utterance of the user and a biological signal of the user, respectively, and the processor may identify the user by extracting characteristic information of the input voice signal and the input biological signal, respectively, and comparing each piece of the extracted characteristic information with the pre-stored characteristic information of the voice signal and the biological signal, respectively.

The voice input unit may include a microphone, and the processor may turn on the microphone based on the biological signal being detected through the electrode.

The biological signal may include at least one of an electromyogram (EMG) signal, an electrooculogram (EOG) signal, an electroencephalogram (EEG) signal, an electrocardiogram (ECG) signal, a galvanic skin response (GSR) signal or a bioelectric impedance analysis (BIA) signal.

The storage may store characteristic information of a synthesis signal in which a voice signal regarding a specific utterance of the user and an EMG signal of a pattern corresponding to the specific utterance are synthesized.

The processor may receive an EMG signal detected through an electrode located near a mouth of the user and generate a synthesis signal in which the input voice signal and the EMG signal are synthesized.

The electronic device may include a display, and the processor may detect an EOG signal of the user and determine whether the user looks a predetermined area on a screen of the display on the basis of the detected EOG signal, and based on the user looking the specific area, identify the user by comparing characteristic information of the generated synthesis signal with characteristic information of the pre-stored synthesis signal.

A controlling method of an electronic device includes receiving a biological signal of a user detected through an electrode and a voice signal of the user detected through a microphone, and identifying the user based on the input biological signal and the input voice signal.

The identifying the user may include generating a synthesis signal in which the input voice signal and the input biological signal are synthesized, and identifying the user based on the generated synthesis signal.

The generating the synthesis signal may include generating the synthesis signal using a voice signal input through the voice input unit while the biological signal is detected and the biological signal.

The electronic device may store characteristic information of a synthesis signal in which a voice signal regarding a specific utterance of the user and a biological signal of the user are synthesized, and the identifying the user may include extracting characteristic information of the generated synthesis signal and identifying the user by comparing the extracted characteristic information with the stored characteristic information of the synthesis signal.

The electronic device may store characteristic information of a voice signal regarding a specific utterance of the user and a biological signal of the user, respectively, and the identifying the user may include extracting characteristic information of the input voice signal and the input biological signal, respectively, and identifying the user by comparing each piece of the extracted characteristic information with the pre-stored characteristic information of the voice signal and the biological signal, respectively.

The receiving may turn on the microphone based on the biological signal being detected through the electrode.

The biological signal may include at least one of an electromyogram (EMG) signal, an electrooculogram (EOG) signal, an electroencephalogram (EEG) signal, an electrocardiogram (ECG) signal, a galvanic skin response (GSR) signal or a bioelectric impedance analysis (BIA) signal.

The electronic device may store characteristic information of a synthesis signal in which a voice signal regarding a specific utterance of the user and the EMG signal of a pattern corresponding to the specific utterance are synthesized.

In addition, the EMG signal may be detected through an electrode located near the mouth of the user.

The controlling method further includes detecting an EOG signal of the user and determining whether the user looks a predetermined area on a screen of the display on the basis of the detected EOG signal, and the identifying the user may include, based on the user looking the specific area, identifying the user by comparing characteristic information of the generated synthesis signal with characteristic information of the pre-stored synthesis signal.

Effect of the Disclosure

According to various embodiments of the disclosure, a user may be identified using at least two signals generated from the user, and thus, the accuracy of user identification may increase in an authentication process.

DETAILED DESCRIPTION

Figure 1A:
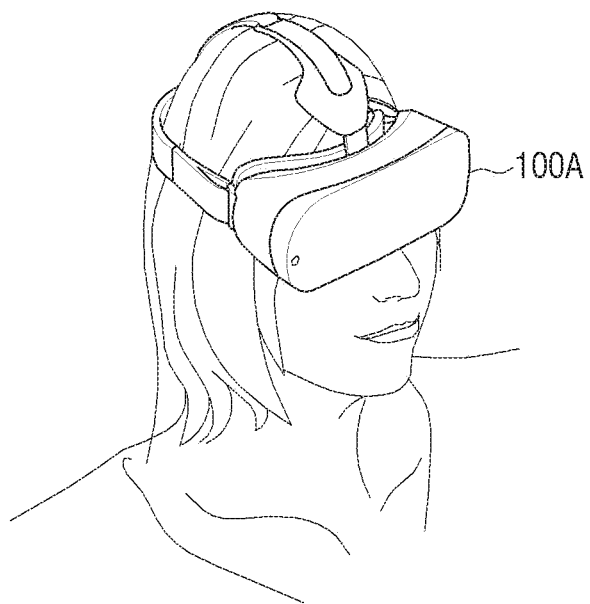
FIG. 1A and FIG. 1B are views illustrating an example of implementation of an electronic device according to an embodiment of the disclosure.

Before specifically describing the disclosure, a method for demonstrating the embodiments and drawings will be described.

With respect to the terms used in an embodiment of the disclosure, general terms currently widely used are selected in view of function with respect to the disclosure. However, these terms may vary depending on intention, legal or technical interpretation, emergence of new technologies, and the like of those skilled in the related art. Also, there may be some terms arbitrarily selected by an applicant. Such terms may be construed according to meanings defined in the disclosure, and may also be construed based on general contents of the disclosure and a typical technical concept in the art unless the terms are not specifically defined.

Also, the same reference numerals or symbols described in the attached drawings denote parts or elements that actually perform the same functions. For convenience of descriptions and understanding, the same reference numerals or symbols are used and described in different embodiments. In other words, although elements having the same reference numerals are all illustrated in a plurality of drawings, the plurality of drawings do not mean one embodiment.

In addition, in order to distinguish between the components, terms including an ordinal number such as "first", "second", etc. may be used in the disclosure and claims. The ordinal numbers are used in order to distinguish the same or similar elements from one another, and the use of the ordinal number should not be understood as limiting the meaning of the terms. For example, used orders, arrangement orders, or the like of elements that are combined with these ordinal numbers may not be limited by the numbers. The respective ordinal numbers are interchangeably used, if necessary.

Also, singular expressions may be interpreted to include plural expressions, unless defined obviously differently in the context. In this specification, terms such as 'include' and 'consist of' should be construed as designating that there are such characteristics, numbers, steps, operations, elements, components or a combination thereof in the specification, but not as excluding in advance the existence or possibility of adding one or more of other characteristics, numbers, steps, operations, elements, components or a combination thereof.

Also, "a module" or "a part" in the disclosure perform at least one function or operation, and these elements may be implemented as hardware or software, or as a combination of hardware and software. Further, a plurality of "modules" or "parts" may be integrated into at least one module and implemented as at least one processor (not shown), except "modules" or "parts" that need to be implemented as specific hardware.

Also, when any part is connected to another part, this includes a direct connection and an indirect connection through another medium. Further, when a certain portion includes a certain element, unless specified to the contrary, this means that another element may be additionally included, rather than precluding another element.

Hereinafter the embodiments of the disclosure will be described in detail with reference to the accompanying drawings.

Figure 1B:
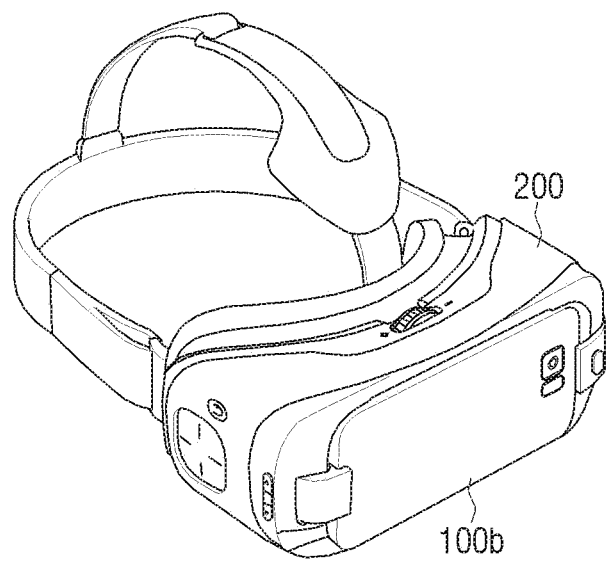

FIG. 1A and FIG. 1B are views illustrating an example of implementation of an electronic device according to an embodiment of the disclosure.

The electronic device 100 of the disclosure may be implemented as an HMD device which may be worn on a head of a user or near eyes such as glasses, for providing VR contents. Here, the electronic device 100 may be implemented as an all-in-one HMD device in which a bend for wearing the apparatus on a head of a user, various user interfaces, and a display, or as a mobile terminal device including a display such as a smartphone and used by being attached to or detached from a separable HMD device (case) without a display.

FIG. 1A illustrates that a user wears the electronic device 100 which is implemented as an all-in-one HMD device 100A. Here, the electronic device 100 may be worn in a form in which a forehead and back of the head are fixed with a band in a Velcro method and block the view regarding an external environment of a user in addition to the content provided from the electronic device 100.

FIG. 1B illustrates an exterior that the electronic device 100 implemented as a mobile terminal device 100B is attached to a separable HMD device 200. As illustrated in FIG. 1B, the electronic device 100 is implemented as a smart phone and provides a display to a user and may be attached to or detached from the body of the separable HMD device 200 which is fixed to the forehead and the back of the head of the user.

The separable HMD device 200 may include an electrode that may detect the biological signal of a user, a button that may receive a user input, a communication module that can communicate with the electronic device 100 in a wired or wireless method, etc. and the detailed configuration of the separable HMD device 200 will be described later.

In the embodiment illustrated in FIG. 1B, the electronic device 100 is not limited to a smartphone. The electronic device 100 may be implemented as various devices including a display such as a tablet personal computer (PC), a mobile phone, a video phone, an e-book reader, a personal digital assistant (PDA), a portable multimedia player (PMP), a MP3 player, a navigation, a camera, etc.

Figure 2A:
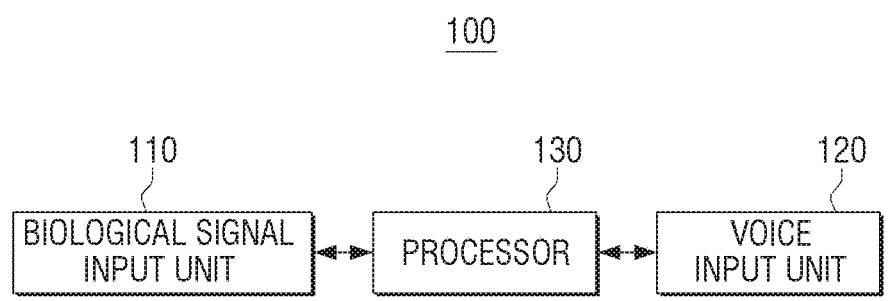
FIG. 2A and FIG. 2B are views illustrating a configuration of an electronic device according to an example of implementation of the disclosure.
Figure 2B:
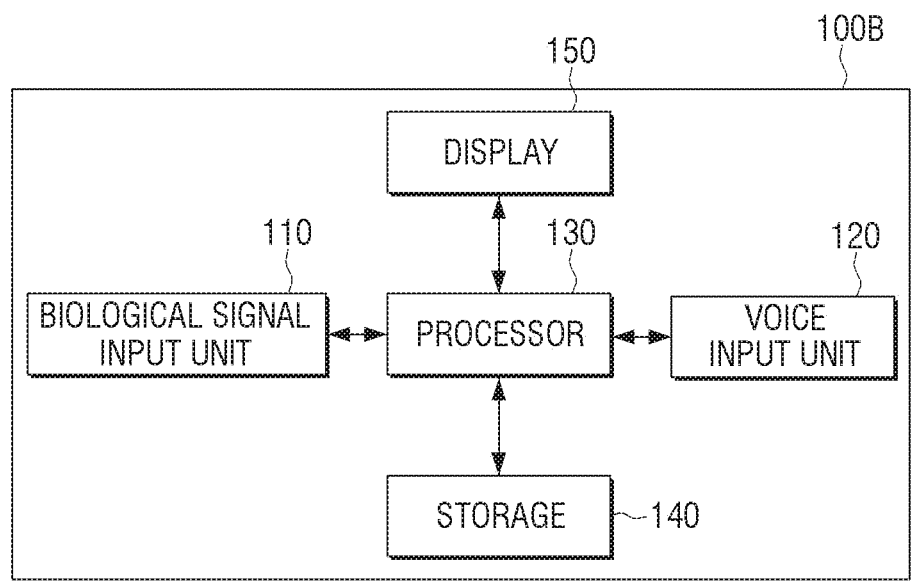
Figure 2B:
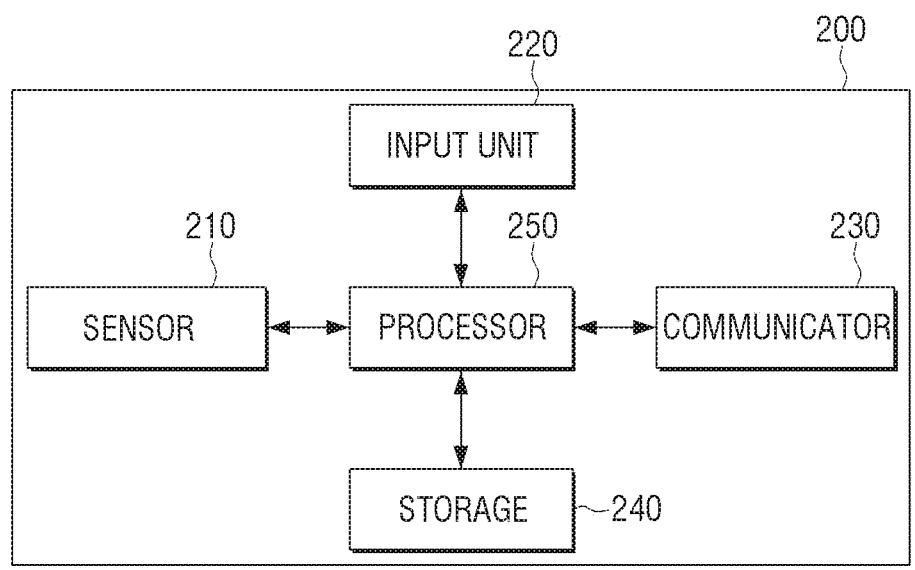

FIG. 2A and FIG. 2B are block diagrams illustrating a brief configuration of an electronic device according to an embodiment of the disclosure.

According to FIG. 2A, the electronic device 100 according to an embodiment essentially includes a biological signal input unit 110, a voice input unit 120, and a processor 130.

The biological signal input unit 110 is a configuration for receiving a biological signal of a user. Here, the user may mean a wearer who wears the electronic device 100, and the biological signal may be obtained from a face of the user which is a part on which the electronic device 100 is mainly put on. Here, the biological signal mainly refers to a bio-electrical signal, and generated by an electrochemical action of excitatory cells which are components of nerve, muscle, glandular tissue. The electronic device 100 may perform a signal process after measuring a desired biological signal using a sensor such as an electrode, etc.

However, the biological signal may be obtained through various parts of user's body other than a face of the user, and may include a signal detected by a physical motion of the user (spinning of a head, nodding, etc.) in addition to the bio electric signal, in a broad sense.

The biological signal as the bio electric signal may be the signal including at least one of an electromyogram (EMG) signal, an electrooculogram (EOG) signal, an electroencephalogram (EEG) signal, an electrocardiogram (ECG) signal, a galvanic skin response (GSR) signal or a bioelectric impedance analysis (BIA) signal.

The EMG signal is a signal that shows a movement of a muscle and an electric signal generated by a movement of the muscle of user's face. The EMG signal is basically generated by measuring an electric signal generated by a physiological change occurs in a muscle fiber membrane. In the embodiment, the EMG signal is an electric signal mainly generated through a movement of a muscle around a mouth when a user speaks or clenches back teeth. The biological signal input unit 110 may receive an electric signal detected from an electrode attached near eyes (especially under eyes) as the EMG signal.

The EOG signal is an electric signal generated according to the movement of eyes due to a voltage difference between corneas of a user. There is a constant electric potential between a cornea (+) and a retina (−) of an eye and the electric potential acts as a constant dipole, and in order to measure this, the biological signal input unit 110 may receive the electric signal detected from the electrode attached right and left of the eye, as the EOG signal. Specifically, if a user gazes a front, a constant dipole is formed between two electrodes, and the output here may be zero (0). If a user gazes left, + component is output, and if a user gazes right, − component is output, and + and − components are changed according to the polarity and the direction of the movement of the electrode. A blinking of user's eyes may be measured using the EOG signal, and the measurement may be performed after attaching the electrode up and down of an eye of one side.

The EEG signal is an electric signal generated when a signal is transmitted from a nerve system to between the brain nerves. The EEG signal is different according to the state of mind and body, and the most important index for measuring the state of activity of a brain. The EEG signal is detected through the electrode attached to a scalp, and the biological signal input unit 110 may receive the electric signal detected from the electrode attached to a forehead as the EEG signal.

The ECG signal is an electric signal generated when a heart contracts and expands and the most representative biological signal that may be easily and quickly measured on a body surface. The exercise of a heart is displayed as beats per minute (bpm) and the change of an autonomic nervous system may be known through the change heart rates. The ECG signal may be measured on user's face and the biological signal input unit 110 may receive an electric signal detected from an electrode attached at various parts as the EOG signal.

The GSR signal is a signal used as an index of an emotional state, and a biological signal for measuring an electric resistance of a skin. For example, there is a feature that an electric resistance of a skin is reduced in a general awareness state, and the GSR signal may indicate the degree of an electric resistance change of the skin according to this feature. That is, the GSR signal relates to the activity of a sweat gland.

The BIA signal is a signal measured in a method that an alternating current flows in a degree that does no harm to a human body, which is a biological signal which can measure an amount of moisture in a body. It is a basic principle of the BIA to estimate a body configuration with an electric resistance measured when a weak alternating current flows at the human body, using the characteristic that a current flows along the parts of which conductivity is the highest. The body fat tissue containing a large amount of moisture has a small resistance even if the conductivity thereof is high, and the body fat tissue containing almost no moisture has low conductivity and has a big resistance, and this characteristic is reflected to the BIA signal.

However, the biological signal may include various types of biological signals in addition to the signals mentioned above.

In addition, the biological signal input unit 110 may further include an electrostatic discharge (ESD) preventing circuit (not illustrated) for preventing the electrostatic discharge phenomenon.

Meanwhile, the biological signal may be detected through an electrode. The biological signal input unit 110 may receive a biological signal detected from at least one electrode in a wired or wireless method, and according to an embodiment, the electrode for detecting the biological signal may be included in the electronic device 100 or separately provided from the electronic device 100.

Specifically, in the embodiment in which the electronic device 100 is implemented as an all-in-one HMD device 100A, at least one electrode may be included in the biological signal input unit 110. In the embodiment in which the electronic device 100 is implemented as a portable terminal device 100B which may be attached to or detached from the separable HMD device 200, at least one electrode may be included in the separable HMD device 200, and the biological signal input unit 110 may receive the biological signal detected from the electrode included in the separable HMD device 200 in a wired or wireless method.

Meanwhile, Ag/AgCl electrode generally used when measuring a biological signal has a nice transmission degree but is not reusable, and there may be various side effects, and thus, in the disclosure, electrolyte is not used between a skin and the electrode, and it is preferable to use a dry type electrode consisting of a metal such as a stainless steel or a copper. The dry type electrode converts a biopotential signal generated by an ion in a body into an electric signal.

Meanwhile, the electrode may include the electrode for detecting a specific single type of biological signal, the electrode for detecting a plurality of types of biological signals (hereinafter referred to as a common electrode), a reference electrode, a ground electrode, etc. The reference electrode may be divided from the ground electrode, respectively, and composed in a form by contacting a body, and the reference electrode and the ground electrode may compose the circuit as the same electrodes. In the embodiment of the disclosure, it will be assumed and described that the reference electrode and the ground electrode are used as the same electrode for convenience. Each electrode may should detect the biological signal near eyes of a user which is the location on which the electronic device 100 is fixed and put on, and thus, the electrode is disposed at the location that contact a peripheral area of eyes in case of the electronic device 100 that is implemented as the all-in-one HMD device 100A or the separable HMD device 200, and may be disposed at different locations according to the type of the biological signal to be detected. The attached location and the function of each electrode will be described below with reference to FIG. 3.

Meanwhile, the voice input unit 120 is an element for receiving a voice from a user. The voice input unit 110 includes a microphone and may collect the voice signal corresponding to the voice uttered by a user. The microphone may generate an electrical voice signal by receiving a voice or a sound from an outside according to the control of the processor 130.

However, the voice input unit 120 may be included in the separable HMD device 200. Here, the voice signal corresponding to the voice uttered by the user may be received from the separable HMD device 200.

Meanwhile, the processor 130 may control an overall operation of the electronic device 100.

Especially, the processor 130 may identify a user based on the biological signal input through the biological signal input unit 110 and the voice signal input through the voice receiver 120. Specifically, the processor 130 may generate the synthesis signal in which the input voice signal and the biological signal are synthesized, and identify a user using the characteristic information of the generated synthesis signal so as to perform a user authentication.

Here, the user authentication is a process for determining whether a user is an entitled user when the user uses the electronic device 100, the user executes a specific application (payment, etc.) or logs in a specific web site.

For this operation, the electronic device 100 may further include a storage 140 storing characteristic information of a synthesis signal in which the voice signal for a specific utterance of a pre-authentic user and a biological signal of the user are synthesized. The processor 130 may extract characteristic information on the synthesis signal in which the input voice signal and the biological signal are synthesized, compare the extracted characteristic information and the characteristic information of the synthesis signal pre-stored in the storage 140, and identify the user. If the entire extracted characteristic information is identical to the pre-stored entire characteristic information, the processor 130 may determine that the user is an entitled user. Here, according to whether the extracted characteristic information and the pre-stored characteristic information have a matching degree exceeding a preset threshold value, whether the user is an entitled user or not may be determined.

Meanwhile, the characteristic information of the synthesis signal may include the characteristic information of the voice signal and the characteristic information of the biological signal. Here, the characteristic information of the voice signal means a specific vector which has a power of discrimination extracted from the voice signal input through the voice input unit 120 when the user utters a specific word or sentence, and is vary according to the specific word or sentence that is uttered.

In addition, the characteristic information of the voice signal may vary according to the tone (waveform) and high and low (frequency), and thus, even if the same word or sentence is uttered, the characteristic information of the voice signal varies according to the user who utters.

Meanwhile, if the voice input unit 120 includes a microphone, if a specific event occurs, the processor 130 may supply a power to a microphone by turning on the microphone, and synthesize the voice signal detected through the microphone thereafter with the biological signal input through the signal input unit 110. Here, the specific event may include, for example, a predetermined voice signal or that a control signal input through a specific button included in the electronic device 100 is input as a trigger signal. In addition, the specific event may include the case in which a specific biological signal is detected when the screen which requires a user authentication (a screen on which a specific application is executed or a lock screen for unlocking of the electronic device 100) is displayed on the electronic device 100. The case in which a biological signal is detected as a specific event will be described later.

Meanwhile, if it is assumed that the biological signal input through the biological signal input unit 110 is an EMG signal, the characteristic information of the EMG signal may be the information on the waveform of the EMG signal having a pattern corresponding to a specific utterance of a user. That is, movement patterns of the peripheral muscle of the mouth according to a specific word or sentence uttered by a user may be included in the characteristic information of the EMG signal.

For example, it may be assumed that "Merry Christmas" is a sentence for an authentication which may assign a proper usage title to a user. If a user utters "Merry Christmas" in the authentication registration stage, the processor 130 may receive a voice signal of "Merry Christmas" through a microphone, and may receive an EMG signal generated by the movement of the peripheral muscle of the mouth according to the utterance of "Merry Christmas" through the biological signal input unit 110.

If the voice signal and the EMG signal are input, the processor 130 may synthesize the voice signal and the EMG signal and store the synthesis signal generated by the synthesis operation or the characteristic information of the synthesis signal in the storage 140. Here, the processor 130 may generate a synthesis signal in which the EMG signal and the voice signal are synthesized, using only the voice signal input through the microphone while the EMG signal is detected. That is, the detection of the EMG signal may be the trigger signal for detecting the voice signal. Accordingly, if the EMG signal detected through the electrode is input through the biological signal input unit 110, the processor 130 may turn-on the microphone. That is, the detection of the EMG signal may be a specific event for turning on the microphone.

Thereafter, in the authentication stage, if a user utters "Merry Christmas", the processor 130 may synthesize the voice signal and the EMG signal which are input according to the corresponding utterance, extract the characteristic information of the synthesized synthesis signal, compare the extracted characteristic information with the characteristic information of the synthesis signal pre-stored in the storage 140 and identify the user.

Accordingly, the processor 130 may perform the user authentication more safely by determining whether the entitled user utters the word or sentence for an authentication ("Merry Christmas") using all of the characteristic information of the voice signal and the EMG signal according to the utterance of the user.

Especially, the synthesis signal generated by synthesizing the voice signal and the EMG signal may include the characteristic information additionally generated by the synthesis of the voice signal and the EMG signal in addition to the characteristic information of the voice signal and the characteristic information of the EMG signal. That is, regarding the waveform of the synthesis signal, the first characteristic information corresponding to the voice signal, the second characteristic information corresponding to the EMG signal, and the third characteristic information additionally generated by the synthesis of the voice signal and the EMG signal may be included. Accordingly, the processor 130 may derive much more characteristic information by synthesizing two signals, and thus, the user may be authenticated more accurately. This will be described in detail with the descriptions of FIG. 5 later.

Meanwhile, according to the above embodiment, if a user voice is not recognized well through the microphone due to a noisy peripheral environment or a small volume of the user voice, a user authentication may be performed by using the characteristic information corresponding to the EMG signal in case of the synthesis signal in which the voice signal and the EMG signal are combined, and thus, the convenience may be improved.

In addition, the starting point and the ending point of the utterance of the user may be simply determined using the time points when the EMG signal is detected and not detected, and thus, the utterance length of the voice signal may be sensed more accurately.

In addition, a user generally moves a mouth muscle first, before an utterance, and thus, the EMG signal is detected earlier than the voice signal. Thus, if the EMG signal equal to or greater than a predetermined threshold value is detected (starting time of the utterance), a microphone is turned on, and if the EMG signal less than a predetermined threshold value is detected (ending time of the utterance), the microphone is turned-off, and accordingly, the microphone should not be maintained as a turn-on state (Always On Mic). That is, the processor 130 may set the detection of the EMG signal as a specific event for turning on the microphone, and according thereto, it is possible that if the user authentication is not performed, the microphone is maintained as a turn-off state, and only when the EMG signal according to the user utterance is detected, the microphone is turned-on, and thus, the power consumption may be reduced.

Meanwhile, as another embodiment, the processor 130 may identify a user by using each piece of characteristic information of the input voice signal and biological signal. Specifically, the storage 140 may store the characteristic information of a voice signal of a specific utterance of a user and the characteristic information of a biological signal of the user, respectively, and the processor 130 may extract each piece of characteristic information of the input voice signal and biological signal, compare each of the extracted piece of characteristic information with the characteristic information of the pre-stored voice signal and the biological signal, and identify the user.

For example, if a user utters "Merry Christmas" in the authentication registration stage, the processor 130 may store the voice signal of "Merry Christmas" or the characteristic information extracted therefrom in the storage 140. In addition, upon the premise that the biological signal input through the biological signal input unit 110 is the EMG signal, the characteristic information of the EMG signal may be extracted from the EMG signal of the pattern corresponding to "Merry Christmas" uttered by a user, and the characteristic information of the extracted EMG signal may be stored in the storage 140.

Thereafter, in the stage performing the authentication, the processor 130 may extract the characteristic information from the voice signal and the EMG signal input through the biological signal input unit 110 and the microphone 120 according to the utterance of the user, respectively, compare each of the extracted characteristic information with the characteristic information pre-stored in the storage 140, and identify the user.

That is, the processor 130 may perform a user authentication by doubly determining whether an entitled user utters an authentication sentence or word ("Merry Christmas"), using the voice signal and the EMG signal.

In addition, even if the characteristic information is pre-stored in the storage 140, the processor 130 may update the pre-stored characteristic information continuously, using the characteristic information extracted from the voice signal input by the user and the EMG signal.

Meanwhile, in the above embodiment, the biological signal has been assumed and described as the EMG signal, but even if the biological signal is a different type of biological signal detected through an electrode such as an EOG signal, an ECG signal, or the like, there would be no problem in implementing the technical idea of the embodiment. For example, if the detected biological signal is an ECG signal, the waveform of the ECG signal may include intrinsic characteristic information for each user, and thus, may be used to determine whether the user is the same user.

In addition, the technical idea of the embodiment may be expanded to the method of performing the user authentication using different types of biological signals (e.g. EMG signal and EOG signal) detected through different electrodes. For example, the electronic device 100 of the disclosure may generate the synthesis signal in which the EMG signal and the EOG signal detected through the different electrodes are synthesized, and perform a user authentication using the characteristic information of the generated synthesis signal.

In addition, the technical idea of the embodiment may be expanded to the method of performing the user authentication using the biological signal and a motion of a user detected through an electrode. For example, the electronic device 100 of the embodiment may generate the synthesis signal in which the EOG signal detected from a user and a motion signal in which the movement of a user's head is detected by detecting the user motion are synthesized, and perform a user authentication using the characteristic information of the generated synthesis signal. Accordingly, for example, only when a user looks a specific location of a display screen or performs a specific operation (blinking, winking, etc.) and moves the head in a specific pattern at the same time, the user may be authenticated as an entitled user.

FIG. 2B is a block diagram illustrating a detailed configuration of the electronic device according to another embodiment of the disclosure.

It is assumed in FIG. 2B that the electronic device 100 implemented as the mobile terminal apparatus 100B is attached to the separable HMD device 200 and executed. The electronic device 100 further includes the storage 140 and the display 150 in addition to the biological signal input unit 110, the voice input unit 120, and the processor 130. The description already provided in FIG. 2A will be omitted.

The separable HMD device 200 may include a sensor 210 which may detect a biological signal of a user, the input unit 220 which may receive a user input, a communicator 230 which may communicate with the electronic device 100 and a storage 240.

The biological signal input unit 110 of the electronic device 100 is an element for receiving a detected biological signal from the separable HMD device 200. As illustrated in FIG. 2B, if the electronic device 100 is implemented as the portable terminal device 100B attached to the separable HMD device 200, the biological signal input unit 110 may include a communication module for communicating with the separable HMD device 200 in a wired or wireless method. The communication with the separable HMD device 200 using the communication module may be performed in various ways. The communication between the electronic device 100 with a separable HMD device 200 may be executed by at least one method of NFC, Wi-Fi, Wi-Fi direct, Zigbee or Bluetooth.

The storage 140 may store various types of data such as an operating system (O/S) software module and various types of multimedia contents including VR contents for driving the electronic device 100. Especially, the storage 140 may store the characteristic information related to the voice signal regarding a specific utterance of the user and a biological signal of the user. The storage 140 may be implemented as one of a hard disk drive (HDD), a solid state drive (SSD), a dynamic random access memory (DRAM) memory, a static RAM (SRAM) memory, a ferroelectrics RAM (FRAM) memory or a flash memory.

The display 150 provides a screen including various contents reusable in the electronic device 100. Here, the contents may include the contents in various formats such as a text, an image, a video, and a graphic user interface (GUI), etc. Especially, the contents may be implemented as a visual reality (VR) contents for providing a 3D image.

The implementation method of the display 150 is not limited, and the display 150 may be implemented as a display in various forms such as a liquid crystal display (LCD), an organic light emitting diodes (OLED) display, an active-matrix organic light-emitting diode (AM-OLED), a plasma display panel (PDP), etc. The display 150 may further include an additional element according to the implementation method thereof. For example, if the display 150 is formed in a liquid crystal method, the display 150 may include an LCD display panel (not illustrated), a black light unit (not illustrated) that provides light thereto, and a panel driving board (not illustrated) driving a panel (not illustrated).

Meanwhile, the electronic device 100 may further include the sensor 160. The sensor 160 may include a first sensor to an n-th sensor for detecting various operations performed in the electronic device 100 and a sensor controller for controlling the first to n-th sensors. For example, a plurality of sensors included in the sensor 160 may include a movement sensor for detecting the movement of the electronic device 100, an iris recognition sensor for recognizing a user's iris as a sensor for a user authentication, a fingerprint recognition sensor for recognizing fingerprints, various sensors for detecting peripheral environment (air pressure, temperature, humidity, illuminance), a user gesture, etc.

The movement sensor may include at least one of an acceleration sensor, a geomagnetic sensor or a gyro sensor. Various sensors included in the movement sensor may detect a three-dimensional movement of the electronic device 100 through one or a combination of more than two of the above sensors.

The acceleration sensor is a sensor for measuring a movement of the electronic device 100 in a space. That is, the acceleration sensor means a sensor detecting the change of the acceleration and/or the change of the angular acceleration generated when the electronic device 100 moves. The acceleration sensor may detect the acceleration in a triaxis direction. In addition, the acceleration sensor may detect that the electronic device 100 is tilted.

The geomagnetic sensor is a sensor for measuring an azimuth. That is, the geomagnetic sensor means a sensor that detects the magnetic field formed in a north and south direction of the earth and measures the azimuth. The geomagnetic sensor may detect the terrestrial magnetism in the triaxis direction. The north direction measured with the geomagnetic sensor may be a magnetic north. However, even if the geomagnetic sensor measures the magnetic north, a true north direction may be output by performing an internal calculation, needless to say.

The gyro sensor is an inertial sensor measuring a rotation angular speed of the electronic device 100. That is, the gyro sensor means a sensor which may know the current direction using the inertial force of a rotating object. The gyro sensor may measure the rotation angular speed in a twinaxis direction.

The movement sensor may sense the movement of the electronic device 100 and recognize the direction to which the electronic device 100 moves, a rotation angular speed, etc.

The sensor controller is an element for controlling the first to n-th sensor at a time, and acts as a sensor hub. According to an embodiment, if the electronic device 100 operates as a sleep mode such as a standby mode, a power saving mode, or the like, the power supplied to the controller 120 is limited, but a minimum power may be supplied to the sensor 150 so that the detection through a sensor module is continuously performed in the sleep mode state. That is, the sensor controller may wake up the processor 130 based on the signal detected through the sensor.

Meanwhile, the sensor 210 of the separable HMD device 200 may include a plurality of electrodes for detecting the biological signal of a user. The plurality of electrodes may include an electrode for detecting various biological signals such as an EMG signal, an EOG signal, an EEG signal, an ECG signal, a GSR signal and a BIA signal as illustrated with regard to FIG. 2A. The plurality of electrodes may be attached to the pad portion which contacts the skin of a user in the separable HMD device 200, and may be attached to an appropriate location according to the type of the biological signal which is to be detected by each electrode on the pad.

The input unit 220 is an element for receiving various inputs of a user, and may include a button or a touch pad which is physically implemented. For example, the input unit 220 may include a call button, a brightness control button, a voice control button, etc., and may be linked with the content displayed on the electronic device 100 and receive an input for playing the content, controlling the function of the content, or the like.

The communicator 230 is an element for communicating with the electronic device 100 in a wired or wireless method, and the descriptions on the configuration and the function of the communicator 230 overlaps with those of the communication module included in the biological signal input unit 110 of the electronic device 100, and thus, the detailed description thereof will be omitted.

The storage 240 is an element for storing the biological signal detected through the sensor 210. In order to receive a plurality of biological signals through one electrode, the processor 250 may control the storage 240 to store the biological signal detected through the electrode.

The processor 250 is an element for controlling the separable HMD device 200 in general. The processor 250 may remove the noise by filtering the biological signal detected through the sensor 210, and determine whether a user is wearing the separable HMD device 200 or whether the user is wearing the device well, based on the characteristic of the detected biological signal. Here, whether the user is wearing on the HMD device 200 may be determined based on various types of biological signals described above and it is not limited specifically, but it is preferable to make a determination based on the EMG signal.

If it is determined that a user is wearing the separable HMD device 200, the wake up signal may be transmitted to the electronic device 100 in a sleep mode. Alternatively, if it is determined that the user is not wearing the separable HMD device 200 well, the signal to output the signal notifying that the device is not worn well may be output (in this case, the separable HMD device 200 may include an LED or a speaker which may provide some notifications to a user) or the signal which notifies that the device is not worn well to the electronic device 100 may be transmitted.

In addition, the processor 250 may measure the quality of a signal of the biological signal detected through the sensor 210 and based on the measured signal quality, the control signal for outputting a warning that the signal quality detected in a specific electrode is bad may be transmitted to the electronic device 100. Alternatively, the processor 250 may output the warning that the signal quality detected in a specific electrode is bad through the LED or the speaker provided on the separable HMD device 200.

Meanwhile, FIG. 2B illustrates the configuration and the operation of the electronic device 100 and the separable HMD device 200 in a case in which the electronic device 100 is implemented as a portable terminal device 100B, but the above operation may be a mere design modification and application to those skilled in the art of the technical field of the disclosure, even if in the case in which the electronic device 100 is implemented as the all-in-one HMD device 100A.

For example, if the electronic device 100 is implemented as the all-in-one HMD device 100A, the configuration and operation of the sensor 210 included in the separable HMD device 200 may be integrated into the sensor 160 of the electronic device 100, and the input unit 220 may be included in the electronic device 100. The storage 240 may be integrated into the storage 140 and the communication module included in the communicator 230 and the biological signal input unit 110 may be omitted. The operation of the processor 250 may be integrated into the operation of the processor 130 of the electronic device 100.

Figure 3:
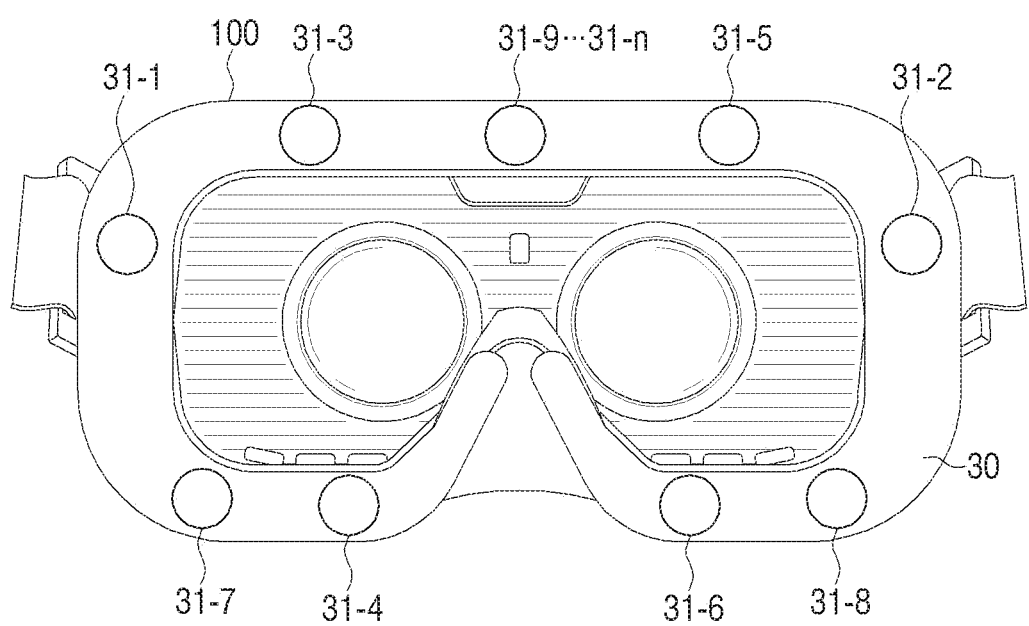
FIG. 3 is a view illustrating each electrode for detecting a biological signal according to an embodiment of the disclosure.

FIG. 3 is a view illustrating each electrode for detecting the biological signal according to an embodiment of the disclosure.

FIG. 3 is a front view seen from the side on which the HMD device 100 is worn. As illustrated in FIG. 3, electrodes 31-1 to 31-*n* which may detect various types of biological signals may be disposed at the contact side 30 which contacts the face of a user near eyes.

Referring to an embodiment shown in FIG. 3, a pair of electrodes 31-1 and 3-2 are attached to a left side and a right side of an eye to detect an EOG signal. The pair of electrodes calculate one electrode change and thus, only one direction from an up and down direction or a left and right direction may be specified. Accordingly, in order to set the direction of an eyeball, two directions of up and down, and left and right may be set, and thus, a pair of electrodes 31-3 and 31-4 for detecting an EOG signal at the part attached to an upper portion of an eye and the part attached to a lower portion of the eye may be provided on the contact side 30. In addition, a pair of electrodes 31-5 and 31-6 for detecting the EOG signal at the part attached to an upper portion of another eye and the part attached to a lower portion of the other eye may be additionally provided.

Accordingly, the processor 130 may specify the left and right directions of an eye through a pair of electrodes 31-1 and 31-2 attached to the left and right sides of the eye, and specify the up and down directions of the eye through the electrodes 31-3 and 31-5 attached to an upper portion of an eye, and the electrodes 31-4 and 31-6 attached to the lower portion of the eye.

Meanwhile, at the lower parts of both eyes, a pair of electrodes 31-7 and 31-8 for detecting the EMG signal may be provided. For one muscle, one electrode is attached and one figure is calculated. The processor 130 may store the intensity of a movement of a muscle according to the size of the input EMG signal by each muscle, and based on the information on the intensity of the movement which is stored, may convert the size of the input EMG signal.

A plurality of electrodes for detecting the EMG signal may be provided in a ring shape near the contact side 30, and the corresponding electrodes may detect the movement of the muscle of an overall face. Especially, the electrode for detecting the EMG signal may be provided on the contact side 30 which is attached to the lower parts of both eyes so as to detect the movement of the muscles near the eyes and a cheekbone according to a mouth shape that mainly changes the shape of a face. That is, it is desirable that the electrode for detecting the EMG signal is disposed near the mouth of a user.

Meanwhile, for detecting the EMG signal, it is preferred to include a reference electrode 31-9 additionally, and the biological signal detected through both electrodes 31-7 and 31-8 and the difference value of the biological signal detected through the reference electrode 31-9 may be used as the EMG signal. The reference electrode 31-9 may be located at the contact side 30 attached to the upper center part of both eyes. However, if a pair of electrodes for detecting the EMG signal are additionally provided and a bi-polar in which the EMG signal is detected using the electric potential difference of a pair of peripheral electrodes is used, the reference electrode 31-9 may not be needed.

Figure 4:
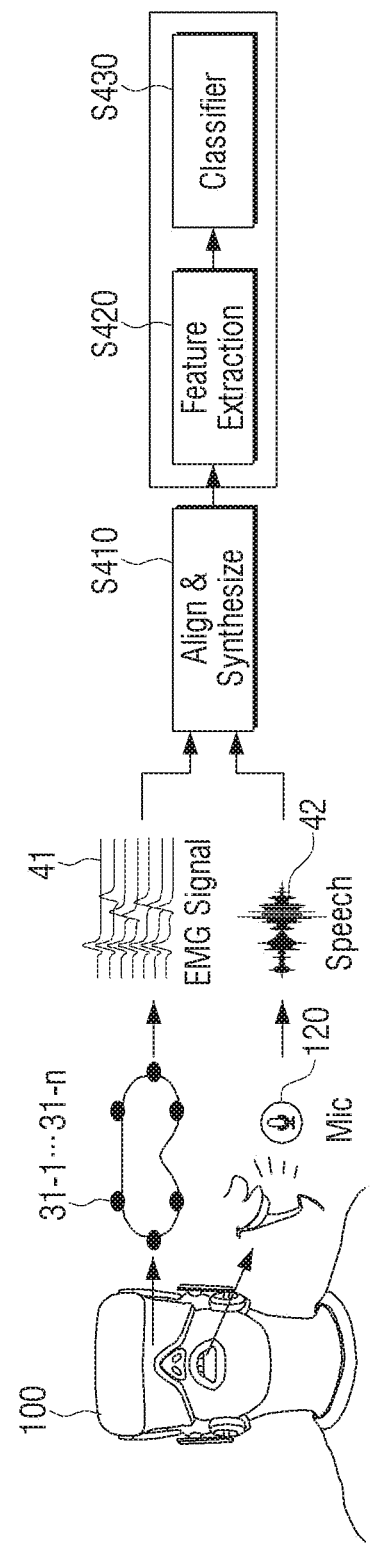
FIG. 4 is a flow chart illustrating a process for performing a user authentication by synthesizing a biological signal detected in an electronic device according to an embodiment of the disclosure.

FIG. 4 is a flowchart for illustrating a process for performing a user authentication by synthesizing the biological signal detected in an electronic device according to an embodiment of the disclosure.

If a user wearing the electronic device 100 utters a predetermined sentence or word to perform a user authentication, the biological signal detected through the electrodes 31-1 to 31-*n* provided in the electronic device 100 is input through the biological signal input unit 110, and the voice signal according to the utterance is input through the voice input unit 120. Here, the biological signal may include various biological signals such as an EOG signal, EMG signal, EEG signal, ECG signal, and the like.

The electronic device 100 of the embodiment illustrated in FIG. 4 may further include the display 150 and the electrodes 31-1 to 31-*n* included in the electronic device 100 may include the electrode for detecting the EOG signal and the electrode for detecting the EMG signal. Here, the processor 130 may determine the location of the pupil of a user based on the EOG signal detected by the electrode for detecting the EOG signal, determine whether a user looks a specific area on the screen of the display 150 according thereto, and perform a user authentication only when it is determined that the user is looking the specific area.

For example, only when it is determined that a user is looking the area displaying the sentence of "User authentication is required" on the screen displayed on the display 150, the processor 130 may perform a user authentication using the voice signal and the EMG signal. This is to prevent performing preprocessing (turning on a microphone, synthesizing the voice signal and the EMG signal, etc.) of a user authentication, because most of the case where a user looks an area other than the area displaying "User authentication is required", may be the case that a user does not want a user authentication or the user authentication is not needed.

In addition, the user's operation of looking the area displaying "User authentication is required" may have an effect of being operated as a trigger operation for performing a user authentication so as to set a time point when a voice according to the utterance is received.

Meanwhile, as illustrated in FIG. 4, the EOG signal and the EMG signal detected through each electrode 31-1 to 31-*n* of the electronic device 100 are converted into the digital signal 41 and 42 by passing through an analog-digital converter (ADC) and the converted signal 41 and 42 may be arranged/synthesized by the processor 130 in operation S410. The processor 130 may extract intrinsic characteristic information from the synthesis signal in which two signals 41 and 42 are synthesized, in operation S420. In the user authentication registration stage, the characteristic information extracted from the synthesis signal in which two signals 41 and 42 are synthesized is stored in the storage 140, and in the stage in which user authentication is performed, the characteristic information of the synthesis signal in which two signals 41 and 42 are synthesized is compared to the characteristic information of the pre-stored synthesis signal, and whether the users are the same is identified.

Figure 5:
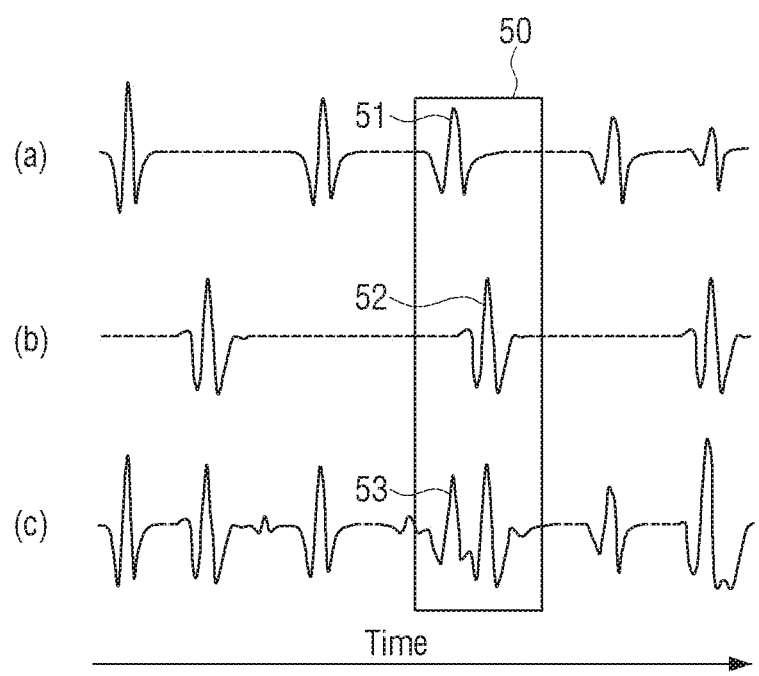
FIG. 5 is a view illustrating a waveform of an EMG signal and a voice signal, and a waveform of a synthesis signal according to an embodiment of the disclosure.

For example, according to the embodiment illustrated in FIG. 5, (a) is a waveform of the EMG signal, (b) is the waveform of the voice signal, and (c) is the waveform of the synthesis signal in which the EMG signal and the voice signal are synthesized. The dotted line of the EMG signal and the voice signal indicates the waveform of the corresponding time section which is omitted and illustrated for convenience.

In a time section 50, if the waveform 51 of the EMG signal and the waveform 52 of the voice signal are synthesized, as the waveform 53 of the synthesis signal, the waveform of a synthesis signal which is in a form of a combination of two waveforms 51 and 52 is generated, and especially, the waveform of the synthesis signal may include the waveform in an intrinsic form generated by the synthesis operation. Accordingly, the characteristic information which may be extracted from the waveform of the synthesis signal may include much information than the characteristic information extracted from each of the waveform 51 of the EMG signal and the waveform 52 of the voice signal.

Meanwhile, in case whether the user is identical is identified according to a machine learning algorithm, the characteristic information extracted from the synthesis signal of two signals 41 and 42 is input to a classifier in operation S430. The characteristic information input to the classifier may be used for training the classifier according to the machine learning algorithm, or determining the sameness of the user by deriving the classification result.

The operations S410, S420, and S430 may be performed by the processor 130 and some operations may be performed by the processor 250 included in the separable HMD device 200.

Figure 6:
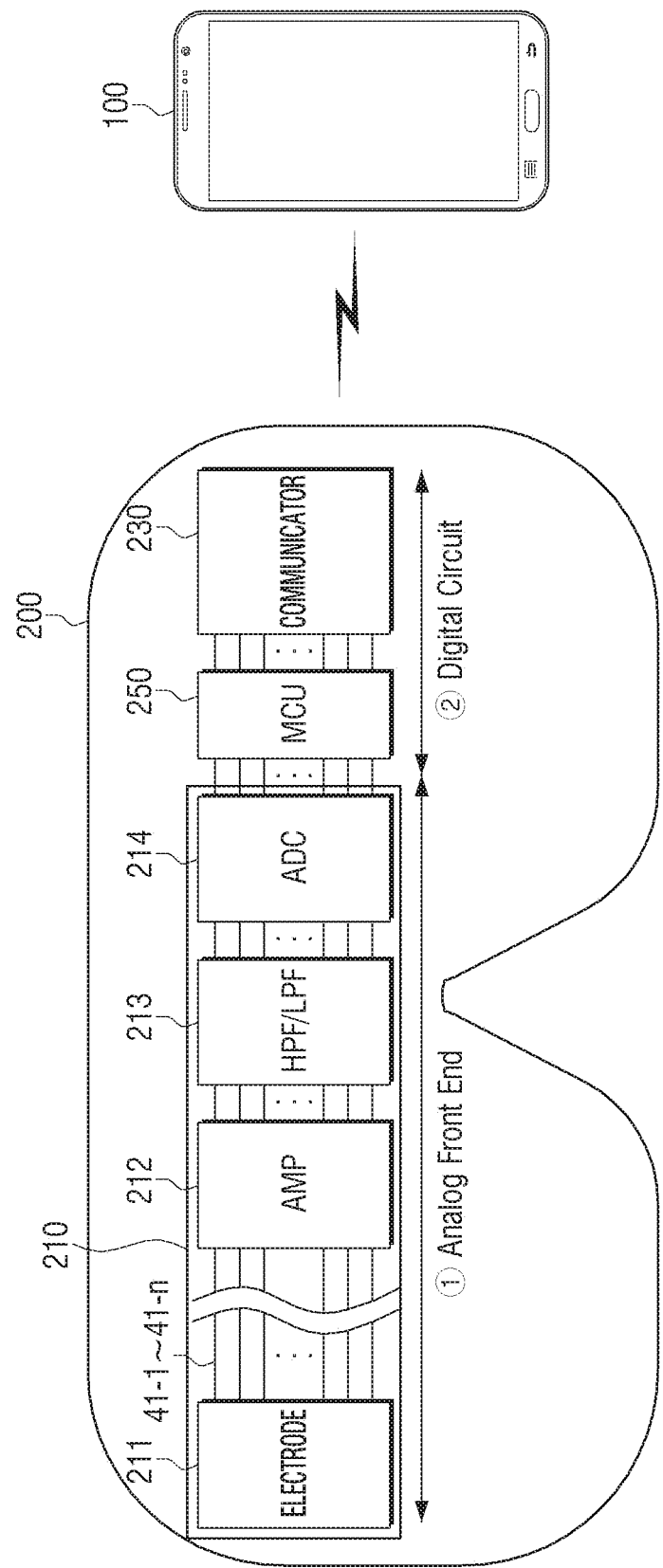
FIG. 6 is a view illustrating each signal flow process in an electronic device according to an embodiment of the disclosure.

FIG. 6 is a view illustrating the flowing process of each signal in an electronic device according to an embodiment of the disclosure.

The embodiment illustrated in FIG. 6 illustrates the progress in which the biological signal detected by the electrode included in the separable HMD device 200 is input to the electronic device 100 realized as a portable terminal device 100B mounted on the separable HMD device 200 and processed.

The biological signal detected from a plurality of electrodes 211 may be transmitted to the terminal device 20 through the channels 41-1 to 41-n corresponding to each electrode. The EMG signal may be converted into a digital signal by passing through the ADC 214. Accordingly, the separable HMD device 200 may be configured by ① an analog front end that processes an analog signal based on the ADC 214 and ② a digital circuit that processes a digital signal which is generated by converting the analogue signal.

① The analog front end includes an operation of the sensor 210. Specifically, the electrode 211 detecting the biological signal, an amplifier (AMP) 212 amplifying the detected biological signal, a high pass filter (HPF)/low pass filter (LPF) 213 for removing the noise of the amplified biological signal, and the ADC 214 for converting the biological signal from which the noise is removed into a digital signal may be included. ② The digital circuit is an element for processing a biological signal which is converted into a digital, and includes a micro controller unit (MCU) 250 performing a filtering through the HPF/LPF and the communicator 230 for transmitting the bio-electric signal to the electronic device 100. In the embodiment illustrated in FIG. 6, the processor 250 is implemented as the MCU.

For example, in a case in which the biological signal is the EMG signal, regarding the electrodes 31-7 and 31-8 used for detecting the EMG signal in FIG. 3, a electric potential difference between the voltage of the EMG signal detected in the muscle of the right side of a face of a user and the reference voltage detected through the reference electrode 31-9 may be identified. The EMG signal including the identified electric potential difference is amplified through the AMP 212 included in the separable HMD device 200 and the noise of the amplified EMG signal may be removed through the HPF/LPF 213 provided in the HMD device 200. Here, the HPF may remove the noise with a direct current component from the amplified EMG signal, and the LPF may remove the noise which is not in the direct current component from the amplified EMG signal.

The EMG signal from which the noise is removed may be converted into a digital signal by passing through the ADC 214, and after passing a high and low pass filtering processes in the MCU 250, transmitted to the communicator 230 and transmitted to the electronic device 100 connected by a communication in real time.

In case of an embodiment in which the communication of the biological signal input unit 110 and the communicator 230 of the electronic device 100 is performed in a wireless method, the biological signal input unit 110 and the communicator 230 may be implemented to perform communication in at least one method among NFC, Wi-Fi, Wi-Fi Direct, Zigbee and Bluetooth, or other various wireless communication methods.

In addition, the embodiment in which the communication of the biological signal input unit 110 and the communicator 230 is performed in a wired method, the biological signal input unit 110 and the communicator 230 may be implemented so as to perform communication in various methods including universal asynchronous receiver/transmitter (UART) method.

Meanwhile, as in the above, the embodiment illustrated in FIG. 6 illustrates the electronic device 100 and the separable HMD device 200 in the embodiment in which the electronic device 100 realized as a portable terminal device 100B is attached to or detached from the separable HMD device 200, and the above disclosure illustrates the operation of the electronic device 100 and the operation of the separable HMD device 200, respectively. However, even in the case in which the electronic device 100 is implemented as the all-in-one HMD device 100A, the technical idea illustrated in FIG. 5 may be applied in the same manner. In this case, the operation of the MCU 250 of the separable HMD device 200 may be performed by the processor 120 of the electronic device 100, and the communicator 230 of the separable HMD device 200 for communicating with the electronic device 100 may be omitted.

Hereinafter an embodiment in which the electronic device 100 of the disclosure is assumed as an all-in-one HMD device will be described unless otherwise described. However, the technical idea of the disclosure provided below may be applied even in the case in which the electronic device 100 is implemented as a portable terminal device which may be attached to or detached from a separable HMD device including a sensor.

Figure 7:
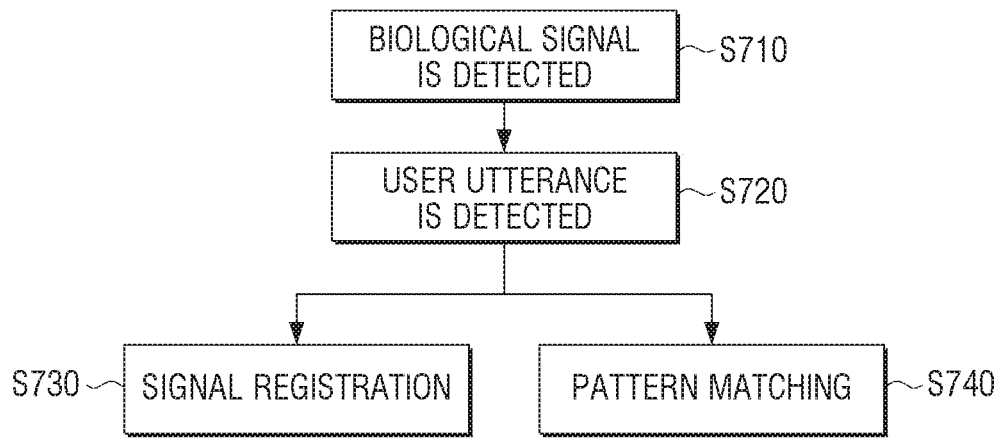
FIG. 7 is a flowchart illustrating a brief operation process of an electronic device according to an embodiment of the disclosure.

FIG. 7 is a flowchart illustrating an operation process of an electronic device briefly according to an embodiment of the disclosure.

The operations of the electronic device 100 may be divided into three major stages. First, a registration operation of the biological signal for a user authentication may be divided into operation S710 in which a biological signal is detected while the electronic device 100 is worn, operation S720 in which a user utterance is detected, and operation S730 in which the detected biological signal and a voice signal are registered. In addition, the operation for performing a user authentication using the biological signal may be divided into operation S710 in which a biological signal is detected while the electronic device 100 is put on, operation S720 in which a user utterance is detected, and operation S740 in which a user authentication is performed by matching the detected biological signal and a voice signal with the pattern of the pre-registered signal.

Specific operations of each stage that configures a registration operation of the biological signal for a user authentication and the operation for performing a user authentication using the biological signal will be described in detail with reference to the flowchart of FIG. 8.

Figure 8:
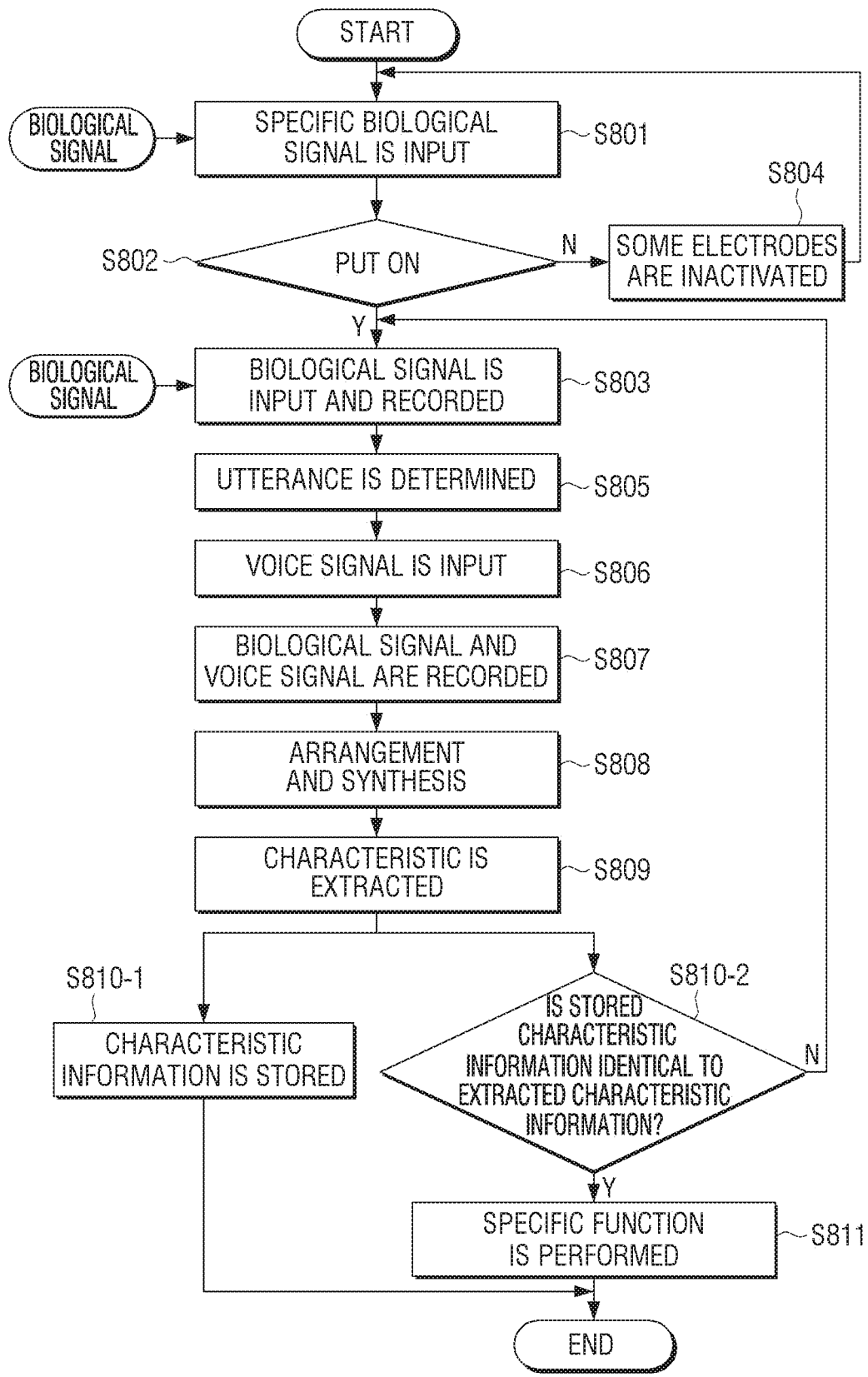
FIG. 8 is a flowchart illustrating a detailed operation process of an electronic device according to an embodiment of the disclosure.

FIG. 8 is a flowchart illustrating an operation process of the electronic device according to an embodiment of the disclosure.

First, in order to determine whether the electronic device 100 is worn, the electronic device 100 may detect and receive a specific biological signal through an electrode for detecting the wearing state of the electronic device 100 in operation S801. Here, it is preferable that the biological signal detected for determining whether the electronic device is worn is the EMG signal, but it is not limited thereto, and whether the electronic device is worn may be determined according to various biological signals. Here, if the electronic device 100 is picked up by a user, the movement of the electronic device 100 may be detected by the movement sensor 160 included in the electronic device 100, and the channel corresponding to the electrode which may detect the EMG signal for determining whether the electronic device 100 is worn may be activated.

If it is determined that the electronic device 100 is put on in operation S802:Y, the electronic device 100 receives a biological signal detected from the electrode and records the input biological signal in operation S803. If it is determined that the electronic device 100 is not worn in operation S802:N, the channel corresponding to some or all electrodes may be inactivated and the power consumption according to the activation of the electrode may be reduced.

In addition, the electronic device 100 may output the result according to the determination regarding the wearing state of the electronic device 100. If the wearing state is bad, a message or a notification voice informing that the electronic device is not worn properly may be output, and if the wearing state is good, a message or a notification voice informing that the electronic device is worn properly may be output.

Meanwhile, here, as a biological signal is input, the electronic device 100 may determine a starting time point of an utterance of a user in operation S805. If the biological signal is the EMG signal, the mouth muscle moves before a user utters so that the EMG signal is detected before a voice signal, and thus, if the EMG signal is detected, the microphone may be turned on.

The voice signal uttered by a user is received through the microphone in operation S806, and the EMG signal and the voice signal which are detected is recorded in operation S807. Two signals are arranged/synthesized in operation S808, and intrinsic characteristic information may be extracted from the synthesized signal in operation S809.

In the user registration stage, the extracted characteristic information may be stored in the storage 140 in operation S810-1, and in the user authentication stage, whether the extracted characteristic information corresponds to the pre-stored characteristic information is determined, and if they corresponds to each other in operation S810-2:Y, a specific function according to a user authentication may be performed in operation S811.

Figure 9A:
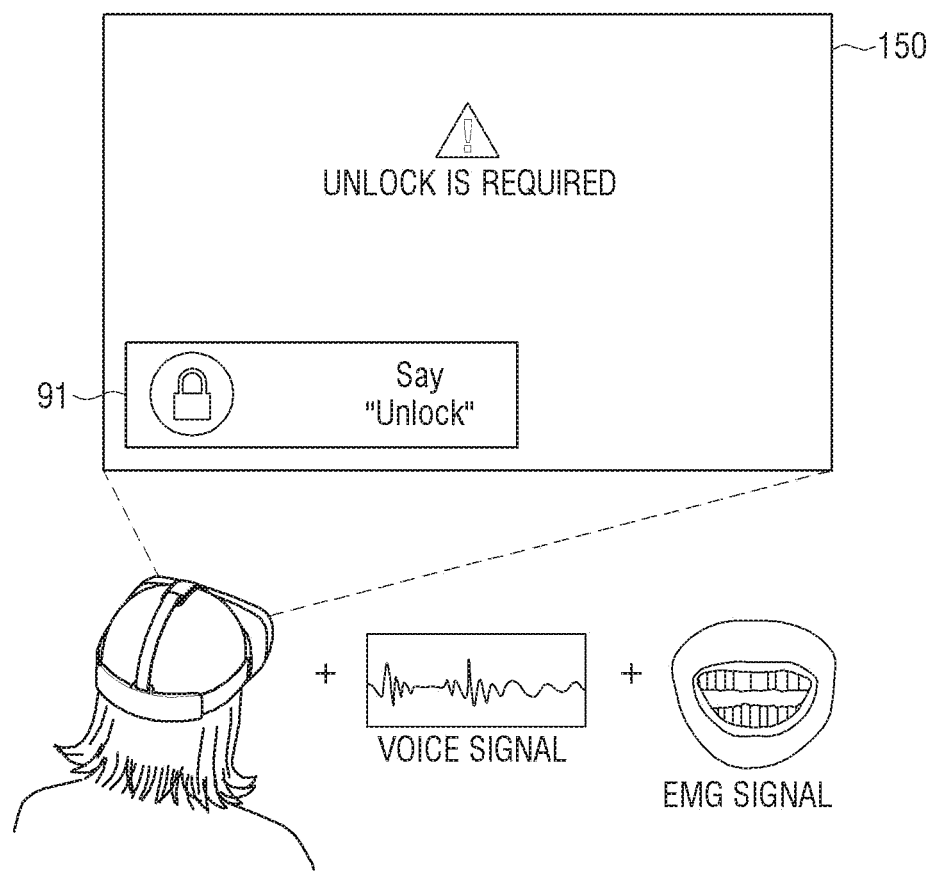
FIG. 9A and FIG. 9B are views illustrating a method for performing a user authentication using an EMG signal and a voice signal according to an embodiment of the disclosure.
Figure 9B:
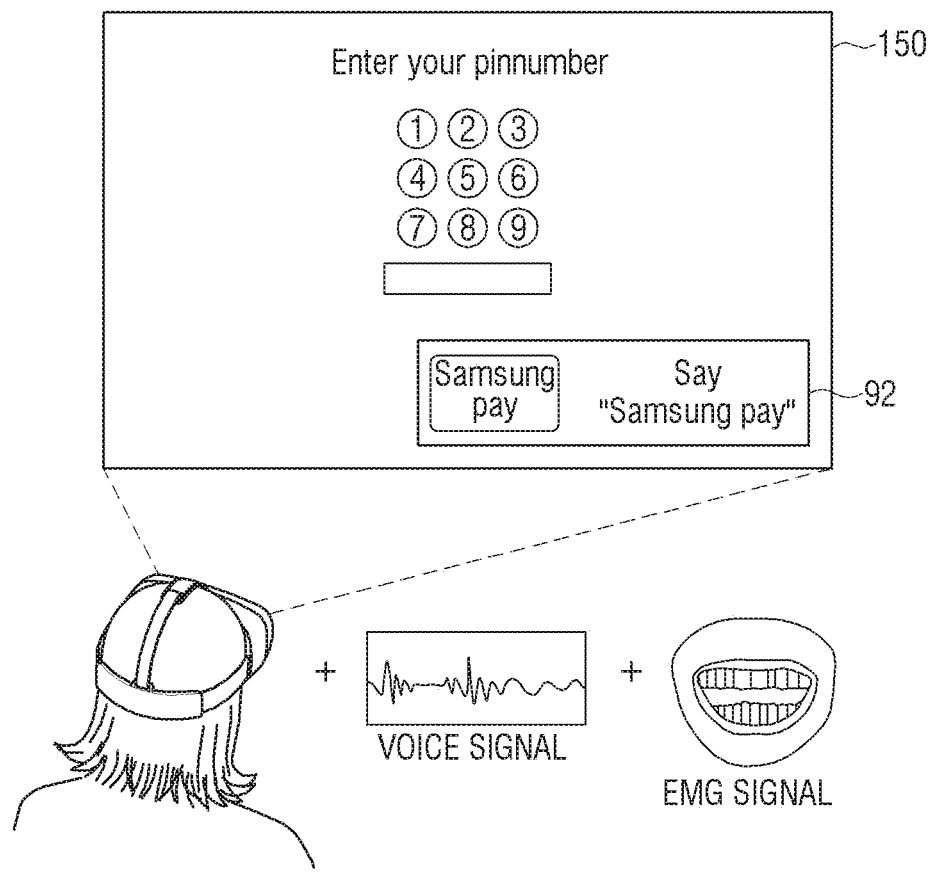

FIG. 9A and FIG. 9B are views for illustrating a method for performing a user authentication using the EMG signal and the voice signal according to an embodiment of the disclosure.

FIG. 9A illustrates an example that if a user wears the electronic device 100 in a lock state, the user unlocks the electronic device 100 only with the utterance of the user. If the user wears the electronic device 100, the processor 130 may control the display 150 to display a message for informing that the electronic device 100 is in the lock state to a user such as "Unlock is required". Here, the informing message may be displayed when the user presses a specific button of the electronic device 100 or a separable HMD device 200, or the informing message may be displayed automatically if it is detected that the electronic device 100 is worn.

Specifically, based on the biological signal detected through the electrode for detecting the wearing state of the electronic device 100 according to a user, the processor 130 may determine the wearing state of the electronic device 100 and if a signal exceeding the threshold value is detected from at least one electrode for detecting the wearing state of the electronic device 100, the processor 130 may determine that the electronic device 100 is in the wearing state.

Meanwhile, the processor 130 may control the display 150 to display the UI 91 inducing the utterance of a user on a location of the displayed screen with the message for informing the lock state. The UI 91 inducing the utterance of a user may be displayed in a form of a message such as "Say unlock".

Here, if a user utters "unlock", the processor 130 may receive a voice signal of the "unlock" through the microphone, and receive the EMG signal generated according to the movement of the muscle near the mouth according to the utterance of "unlock" through the biological signal input unit 110.

The processor 130 may synthesize the voice signal and the EMG signal input according to the corresponding utterance, extract the characteristic information of the synthesized synthesis signal, compare the extracted characteristic information with the characteristic information of the synthesis signal of the voice signal and the EMG signal of a user corresponding to "unlock", which are pre-stored in the storage 140, and identify the user. If the similarity according to the comparison result exceeds a predetermined threshold value, the processor 130 may determine that the current user is an entitled user and unlock the electronic device 100.

In addition, the processor 130 may determine the location of the user's pupil based on the EOG signal detected by the electrode for detecting the EOG. According thereto, the processor 130 may determine whether a user looks the area in which the UI 91 inducing the utterance of a user is displayed on the screen of the display 150, and may determine the user is an entitled user only when it is determined that the user looks the corresponding area.

As another embodiment, FIG. 9B illustrates an example in which an electronic payment is performed only with a user utterance rather than a pin number.

If a user buys a content through a specific application or a web site, for the electronic payment, the pin number for a user authentication may be required to be input. Here, the processor 130 may control the display 150 to display the UI 92 inducing the user's utterance on one location of a displayed screen. The UI 92 inducing the user's utterance may be displayed in a form of a message such as "Say Samsung Pay".

Here, if a user utters "Samsung Pay", the processor 130 may receive a voice signal of "Samsung Pay" through the microphone, and may receive the EMG signal generated by the movement of the muscle near a mouth according to the utterance of "Samsung Pay" through the biological signal input unit 110.

The processor 130 may synthesize the voice signal and the EMG signal input according to the utterance, extract the characteristic information of the synthesized synthesis signal, compare the extracted characteristic information with the characteristic information of the synthesis signal of the user's voice signal and the EMG signal corresponding to "Samsung Pay" which is pre-stored in the storage 140, and identify the user. If the similarity according to the comparison result exceeds a predetermined threshold value, the processor 130 may determine that the current user is an entitled user and approve the electronic payment.

In addition, as the embodiment of FIG. 9A, the processor 130 may determine the location of user's pupil based on the EOG signal detected by the electrode for detecting the EOG signal. According thereto, the processor 130 may determine whether a user looks the area on which the UI 92 inducing the user's utterance is displayed on the screen of the display 150 and determine that the user is entitled only when the user looks the corresponding area.

With regard to the embodiment of FIG. 9B, the system in which the electronic device 100 transmits authentication information to the server providing an application or a web site for an electronic payment will be described in more detail in FIG. 12.

Figure 10:
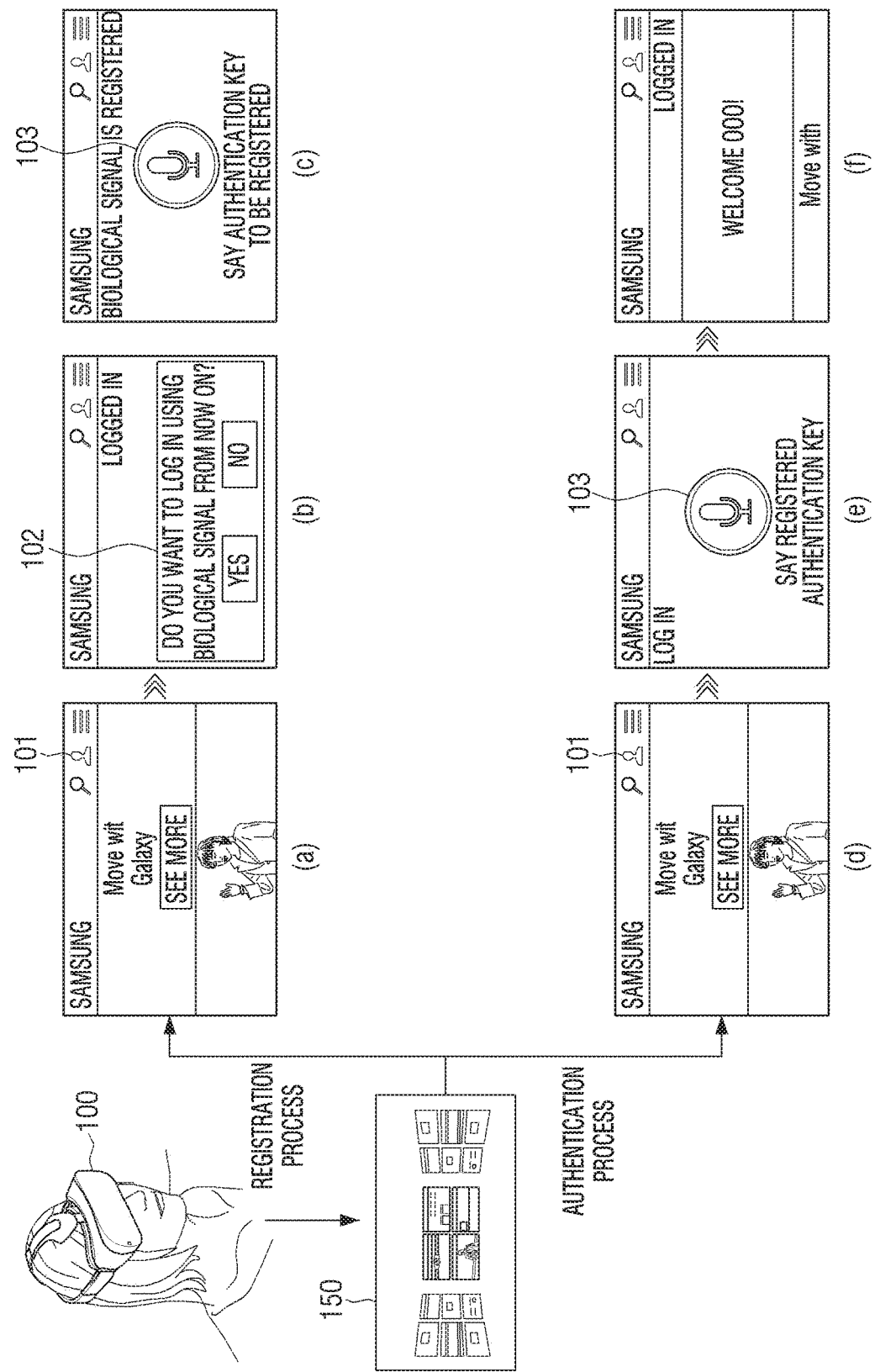
FIG. 10 and FIG. 11 are views illustrating a user authentication method using a biological signal in a web site according to an embodiment of the disclosure.
Figure 11:
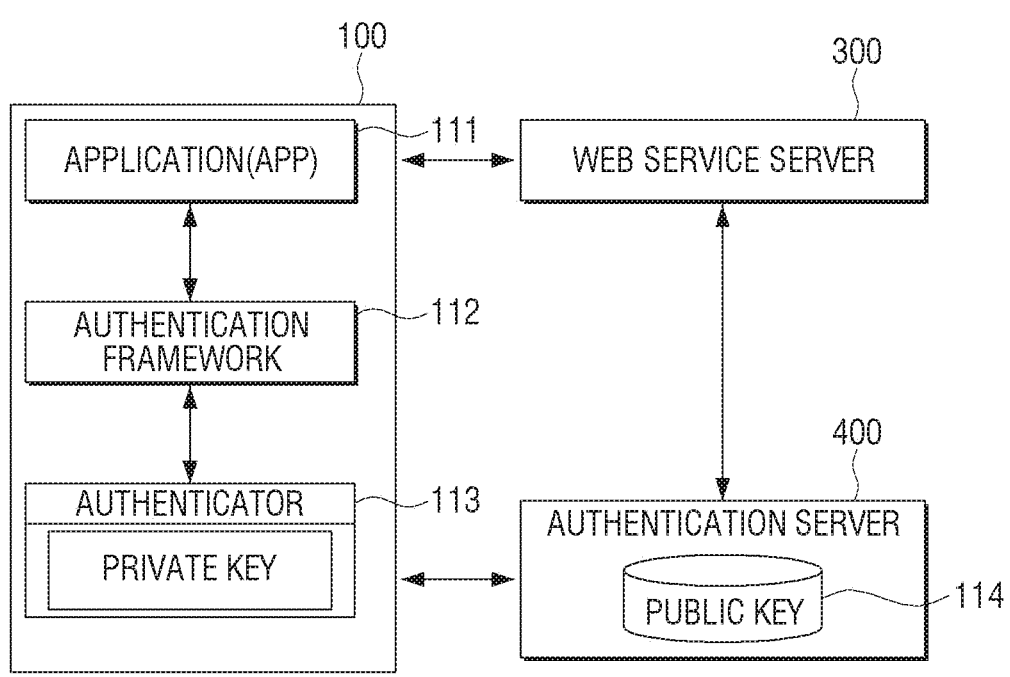

FIG. 10 and FIG. 11 are views illustrating a user authentication method using a biological signal in a web site according to an embodiment of the disclosure.

Currently, most of web services authenticate a user using an ID and a password and allows an access to personal information, but the password may incur the personal information leakage and may be inconvenient for a user, and thus, a new authentication technology such as a Fast Identity Online (FIDO) which authenticate a user without using a password has been introduced.

Especially, as a body-based authentication method utilizing the action using the body structure or a body of a user such as a face recognition, an iris recognition, a finger print recognition, etc., has been introduced, the security and a convenience have been supplemented. FIG. 10 illustrates a method for logging in a user account of a web site using a biological signal and a voice signal when accessing the web site using the electronic device 100.

As illustrated in FIG. 10, the method for logging in a user account of the web site using the biological signal and the voice signal may be divided into a registration process for registering a biological signal and a voice signal of a user, and an authentication process in which a user authentication is performed by uttering a biological signal and a voice signal by a user.

In the registration process, first, the user may perform a general user registration using an ID and a password by accessing the web site as illustrated in (a) of FIG. 10. Thereafter, if a log in is performed for the first time by selecting the user log in UI 101 of the web site, the message 102 such as "Do you want to log in using a biological signal from now on?" as illustrated in (b) of FIG. 10 may be displayed. If a user selects "yes", the biological signal registration screen such as (c) of FIG. 10 is displayed, and the UI 103 indicating that a recording is available and a notification message such as "Say an authentication key to be registered" may be displayed. If the user utters the authentication key to register, the voice signal corresponding to the uttered authentication key and the EMG signal detected through the electrodes near the mouth may be registered in the electronic device 100. Here, the electronic device 100 may generate a pair of private key and a public key corresponding to the registered voice signal and the EMG signal and thereafter, transmit the public key to a web site.

Specifically, in the authentication process, if a user selects a user log in UI 101 of a web site as illustrated in (d) of FIG. 10 first, as illustrated in (e) of FIG. 10, the message 103 such as "Say the registered authentication key" may be displayed. If the user utters the registered authentication key, the electronic device 100 may perform a user authentication by comparing the voice signal corresponding to the uttered authentication key and the EMG signal detected through the electrode near the mouth, with the voice signal and the EMG signal registered in the storage 140. If the user authentication is completed, the electronic device 100 transmits the public key to a web site, and as illustrated in (f) of FIG. 10, the log in is lastly completed in the web site.

FIG. 11 is a block diagram illustrating a method for performing an authentication through an authentication server when accessing a web site or a web application.

The electronic device 100 may perform communication with the web service server 300 that services a web site or a web application and the authentication server 400 that performs a user authentication, through the communicator 165. The communicator 165 may include the first communicator 166 for performing a communication with the web service server 300 and the second communicator 167 for performing a communication with the authentication server 400. However, the authentication server 400 may be the server included in the web service server 300.

Here, the user authentication of the electronic device 100 and the authentication server 400 may be performed by a protocol according to a fast identity online (FIDO) authentication method.

First, if a user executes an application 111 of the electronic device 100, accesses the web service server 300, and perform a registration operation for registering the voice signal and biological signal of the user, in an authentication framework 112, the synthesis signal (authentication token) in which a voice signal and a biological signal of a user are synthesized passes through an encryption process, and the intrinsic private key 113 and public key 114 corresponding to the corresponding synthesis signal are generated, respectively. The authentication framework 112 stores and manages the private key 113 in a secure entity in the electronic device 100 which is secure and transmits the public key 114 to the authentication server 400. If the electronic device 100 transmits the public key 114 to the authentication server 400, the authentication server 400 registers the public key 114.

The user accesses the web service server 300 again and tries a user authentication (try logging in through an utterance, etc.), the web service server 300 requests an authentication to the authentication server 400, and the authentication server 400 transmits a challenge value to the electronic device 100 together with the policy regarding the user. The electronic device 100 performs an electronic signature on the challenge value using the private key 113 stored in the security entity, and transmits the challenge value to which the electronic signature is performed to the authentication server 400. The authentication server 400 may complete the user authentication by verifying the signed challenge value with the public key 114 of a user. If the authentication server 400 transmits user authentication information to the web service server 300, the web service server 300 may confirm that the user is authenticated and provide various services (log in, content playback, electronic payment, etc.) according to a user authentication to the electronic device 100.

Figure 12:
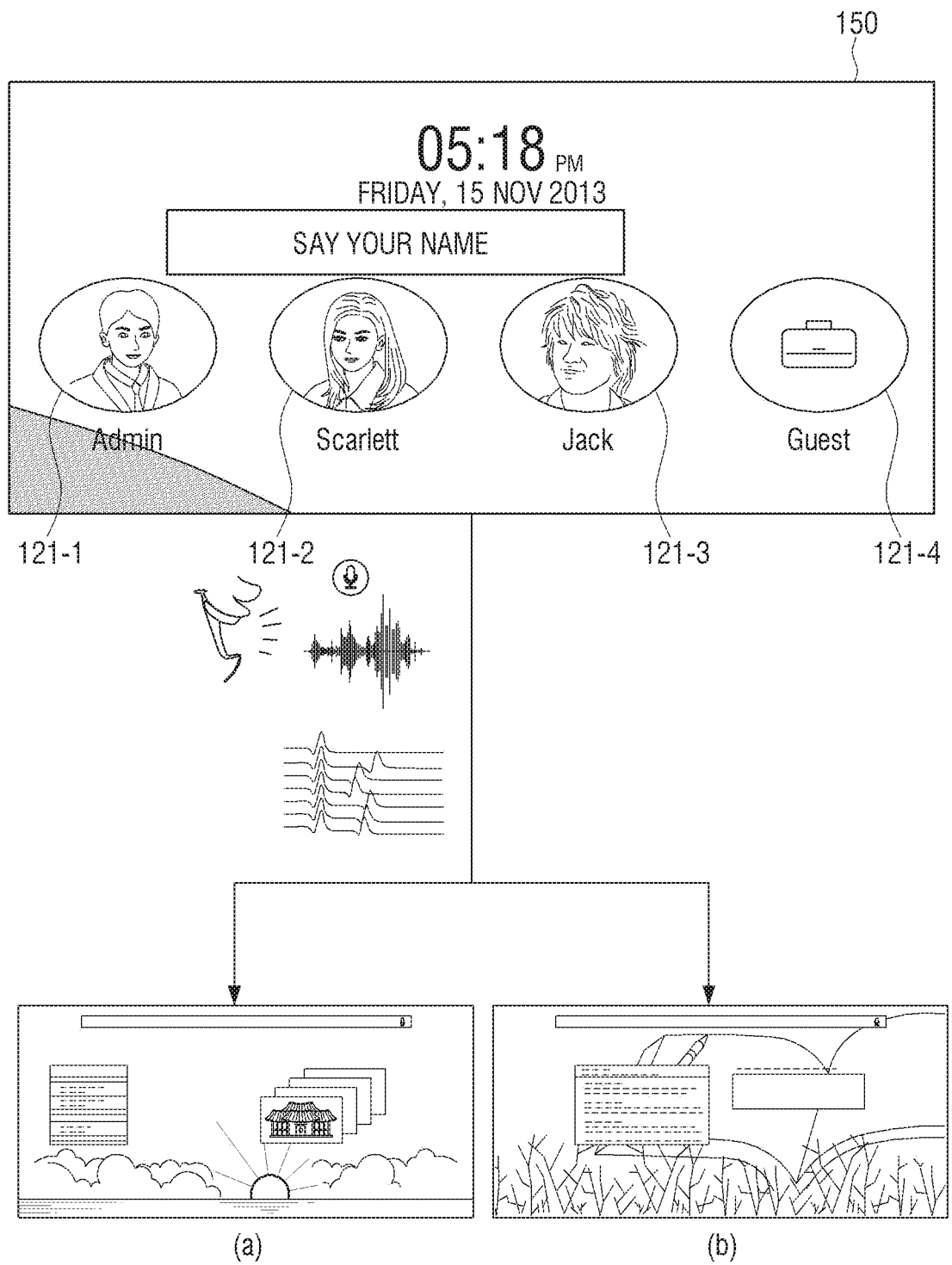
FIG. 12 is a view for selecting one of a plurality of registered users using a biological signal according to an embodiment of the disclosure.

FIG. 12 is a view for selecting one of a plurality of registered users using a biological signal according to an embodiment of the disclosure.

If the electronic device 100 allows an access by multiple users, the electronic device 100 may provide a user environment (customized home screen, account, application, setting, etc.) corresponding to the profile of the authenticated user based on the biological signal.

As illustrated in FIG. 12, the display 150 may display a user selection screen on which a log in may be performed with one of a plurality of users registered in the electronic device 100. The user selection screen may display the UI 121-1 to 121-3 for selecting each of registered users, and the UI 121-4 for logging in as a guest.

The storage 140 of the electronic device 100 may store characteristic information of the voice signal uttered by each user the EMG signal corresponding to each voice signal, and usage environment information corresponding to each user, so as to correspond to the name of each user. If a user utters his/her name, the processor 130 may authenticate the user by detecting the voice signal and the EMG signal corresponding to the corresponding utterance and comparing the signals with the stored characteristic information, and may load and provide the usage environment according to the pre-stored profile of the authenticated user (refer to (a) and (b) of FIG. 12).

Figure 13:
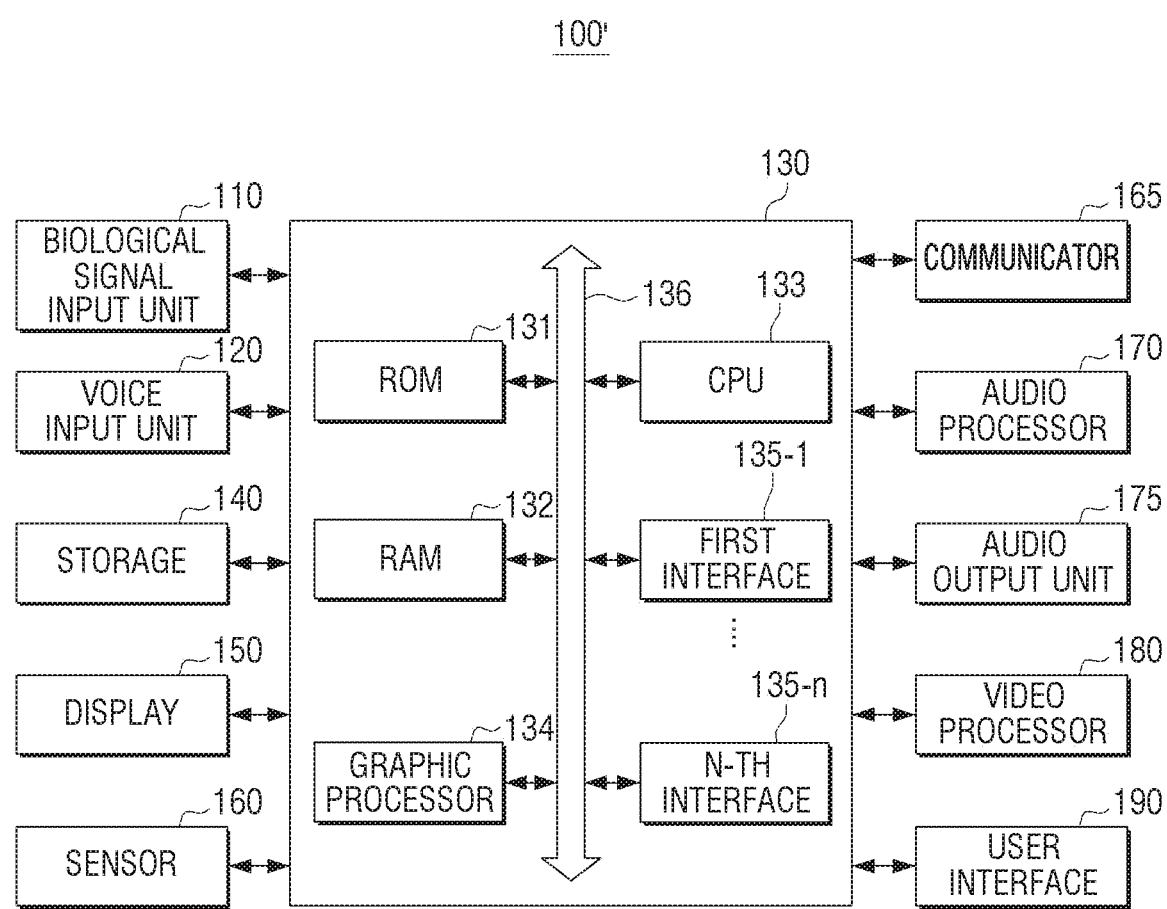
FIG. 13 is a block diagram illustrating a detailed configuration of an electronic device according to an embodiment of the disclosure.

FIG. 13 is a block diagram illustrating a configuration of an electronic device in detail.

As illustrated in FIG. 13, the electronic device 100' according to another embodiment of the disclosure may include the biological signal input unit 110, the voice input unit 120, the processor 130, the storage 140, the display 150, the sensor 160, an audio processor 170, an audio output unit 175, a video processor 180, and a user interface 190. Hereinafter the overlapping description with the descriptions of FIG. 2A and FIG. 2B will be omitted.

The processor 130 may include a ROM 131, a RAM 132, a CPU 133, a graphic processor 134, a first interface 135-1 to n-th interface 135-*n*. The ROM 131, the RAM 132, the CPU 133, the graphic processor 134, the first interface 135-1 to n-th interface 135-*n* may be connected to each other through a bus 136.

The CPU 133 accesses the storage 140 and performs a booting using the O/S stored in the storage 140. In addition, the CPU 133 may perform various operations using various programs, contents, data, etc.

The ROM 131 may store a command set for system booting. When a turn-on command is input and thus a power is supplied, the CPU 133 may copy the O/S stored in the storage 40 to the RAM 132 according to the instructions stored in the ROM 131, and boot the system by executing the O/S. When the booting is completed, the CPU 133 copies various application programs stored in the storage 140 to the RAM 132, and executes the application programs copied in the RAM 132 to perform various operations.

The graphic processor 134 may generate a screen including various objects such as an icon, an image, a text, etc. using a calculator (not illustrated) and a renderer (not illustrated). The calculator may compute attribute values, such as coordinate values, shapes, sizes, and colors of the objects, according to a layout of the screen. The renderer may generate a screen including the objects in various layouts based on the attribute values computed by the calculator.

The first interface 135-1 to n-th interface 135-*n* may be connected to the above described various elements. One of the interfaces may be a network interface which is connected to an external apparatus through a network.

Meanwhile, the operation of the processor 130 described above may be performed by executing the program stored in the storage 140.

The storage 140 may store an O/S software module for driving the electronic device 100' and various types of data such as various forms of multimedia contents.

Specifically, the storage 140 may store the base module processing the signal transmitted from each hardware included in the electronic device 100', a storage module managing the databased (DB) and a registry, a graphic processing module for generating a screen of a layout, a secure module, etc.

The display 150 provides a screen including various contents which may be reproduced in the electronic device 100'. Here, the contents may include a content in various formats such as text, image, video, graphic user interface (GUI), etc. Especially, the contents may be implemented as a VR contents for providing a 3D image.

The sensor 160 is a configuration for detecting various operations performed in the electronic device 100'. The detailed configuration of the sensor 160 has been described in FIG. 2B, and thus, the description thereof will be omitted.

The communicator 165 is a configuration communicating with an external apparatus according to various types of communication methods. The communicator 165 may transmit or receive data with an external apparatus according to various communication standards such as a near field communication (NFC) method, ZigBee, digital living network alliance (DLNA), Wi-Fi, Bluetooth, long term evolution (LTE), etc. Alternatively, the communicator 165 may transmit or receive data with an external apparatus by being connected in a wired/wireless network including an internet network.

The communicator 165 may include various communication chips such as a Wi-Fi chip, a Bluetooth chip, a wireless communication chip, etc., to communicate with an external apparatus based on the above described communication methods, and communicate with another electronic device including a server using the corresponding chips. In addition, the communicator 165 may include a wired communication chip, a wired communication terminal, etc. for communicating with an external apparatus through a wired communication method.

The audio processor 170 is an element for processing audio data.

The audio output unit 175 is an element for outputting an audio processed from the audio processor 170.

The video processor 180 is an element that performs various types of image processing, such as decoding, scaling, noise filtering, frame rate converting, resolution converting, etc., with respect to a content.

The user interface 190 is an element for detecting a user interaction for controlling an overall operation of the electronic device 100". The user interface 190 may include various interaction detection apparatuses such as a microphone (not illustrated), a camera (not illustrated), etc.

Figure 14:
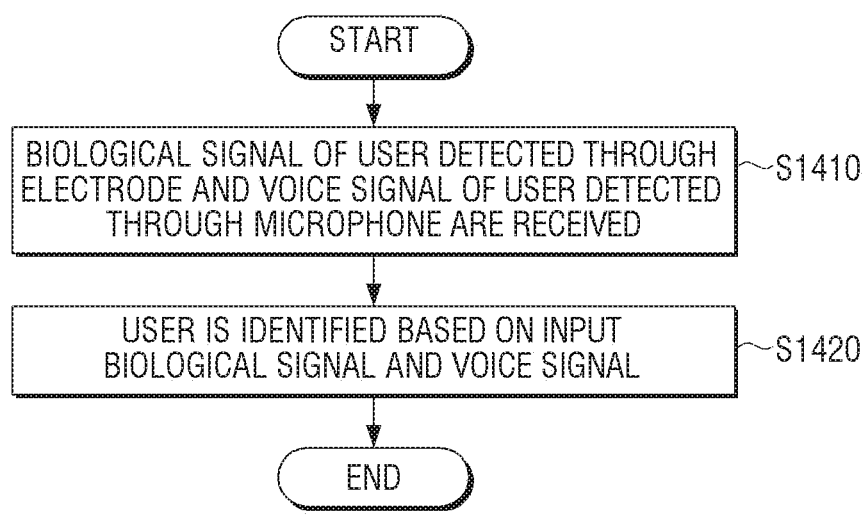
FIG. 14 is a flowchart illustrating a controlling method of an electronic device according to an embodiment of the disclosure.

FIG. 14 is a flowchart illustrating a controlling method of an electronic device according to an embodiment of the disclosure.

First, a biological signal of a user detected through an electrode and a voice signal of a user detected through a microphone are received in operation S1410. Here, if the biological signal is detected through an electrode, the microphone may be turned on.

Thereafter, a user is identified based on the input biological signal and voice signal in operation S1420.

Here, a synthesis signal, in which the input biological signal and the voice signal input through the microphone while the biological signal is detected are synthesized, may be generated, and a user may be identified based on the generated synthesis signal.

For this operation, the electronic device may store the characteristic information of the synthesis signal which is generated by synthesizing the voice signal regarding a specific utterance of a user and the biological signal of a user, and the user may be identified by extracting the characteristic information of the generated synthesis signal and comparing the extracted characteristic information with the characteristic information of the stored synthesis signal. For example, if the similarity between the extracted characteristic information and the characteristic information of the stored synthesis signal is equal to or greater than a predetermined threshold value, the user may be determined as an entitled user.

According to various embodiments of the disclosure as described above, the user authentication is performed using the biological signal of a user in addition to the voice signal, and thus, the accuracy of a user identification increases. Especially, much more characteristic information may be extracted from a synthesis signal in which the voice signal and the biological signal of a user are synthesized, and thus, the accuracy of the user identification may increase.

In addition, in a case in which it is difficult to perform a voice recognition in a noisy environment, the user authentication may be performed using the biological signal, and thus, the vulnerability of the voice recognition regarding the noise of a peripheral environment may be supplemented.

In addition, the biological signal of a user who wears an electronic device is also detected and used to perform a user authentication, and thus, the security issue that the user authentication is performed by the voice uttered by a person other than the user who is wearing the electronic device, may be solved.

The controlling method according to various embodiments described above may be implemented as a program and stored in various recording medium. That is, a computer program which is processed by various processors to execute the above-described various controlling methods may be stored and used in a recording medium.

For example, a non-transitory computer readable medium storing the program performing receiving a biological signal of a user detected through an electrode and a voice signal of a user detected through a microphone, and identifying a user based on the input biological signal and voice signal may be provided.

The non-transitory computer readable medium is not a medium that stores data for a short moment such as a register, a cash and a memory and the like, but a medium that stores data semi-permanently and which is readable by an apparatus. In detail, the above-described various applications or programs may be stored in the non-transitory computer readable medium, for example, a compact disc (CD), a digital versatile disc (DVD), a hard disc, a Blu-ray disc, a universal serial bus (USB), a memory card, a read only memory (ROM), and the like, and may be provided.

Although various embodiments of the disclosure have been illustrated and described hereinabove, the disclosure is not limited to the above-mentioned embodiments, but may be variously modified by those skilled in the art to which the disclosure pertains without departing from the scope and spirit of the disclosure as set forth in the accompanying claims. These modifications should also be understood to fall within the scope of the disclosure.

The invention claimed is:

1. An electronic device comprising:
a biological signal input unit configured to receive a biological signal of a user detected through an electrode;
a voice input unit configured to receive a voice signal of the user;
a memory; and
a processor configured to:
generate a first synthesis signal in which the received voice signal and the received biological signal are synthesized,
obtain first characteristic information from the first synthesis signal,
obtain second characteristic information from a second synthesis signal in which a voice signal regarding a specified utterance of the user and a specified biological signal of the user are synthesized, and
identify the user based on the first characteristic information and the second characteristic information.

2. The electronic device as claimed in claim 1, wherein the processor generates the first synthesis signal using the received voice signal and the received biological signal while the biological signal is detected.

3. The electronic device as claimed in claim 1, wherein the memory is configured to store the second characteristic information of the second synthesis signal.

4. The electronic device as claimed in claim 3, wherein the specified biological signal is an EMG signal of a pattern corresponding to the specified utterance of the user.

5. The electronic device as claimed in claim 4, wherein the electrode is configured to be located near a mouth of the user, and
wherein the processor
receives the EMG signal, wherein said EMG signal is detected through the electrode, and
generates the first synthesis signal in which the received voice signal and the EMG signal are synthesized.

6. The electronic device as claimed in claim 5, further comprising:
a display,
wherein the processor is further configured to:
detect an EOG signal of the user and determine whether the user looks at a predetermined area on a screen of the display based on the detected EOG signal, and
based on the user looking at the predetermined area, identify the user by comparing the first characteristic information of the first synthesis signal with the second characteristic information of the second synthesis signal.

7. The electronic device as claimed in claim 1,
wherein the voice input unit includes a microphone; and
wherein the processor turns on the microphone based on the received biological signal being detected through the electrode.

8. The electronic device as claimed in claim 1, wherein the received biological signal includes at least one of an electromyogram (EMG) signal, an electrooculogram (EOG) signal, an electroencephalogram (EEG) signal, an electrocardiogram (ECG) signal, a galvanic skin response (GSR) signal or a bioelectric impedance analysis (BIA) signal.

9. A method comprising:
receiving a biological signal of a user detected through an electrode;
receiving a voice signal of the user detected through a microphone;
generating a first synthesis signal in which the received voice signal and the received biological signal are synthesized;
obtaining first characteristic information from the first synthesis signal;
obtaining second characteristic information from a second synthesis signal in which a voice signal regarding a specified utterance of the user and a specified biological signal of the user are synthesized; and
identifying the user based on the first characteristic information and the second characteristic information.

10. The method as claimed in claim 9, wherein the generating of the first synthesis signal comprises generating the first synthesis signal using the received voice signal and the received biological signal while the biological signal is being received.

11. The method as claimed in claim 9,
wherein the second characteristic information of the second synthesis signal is stored in an electronic device.

\* \* \* \* \*